(12) United States Patent
Viscomi et al.

(10) Patent No.: US 8,765,778 B2
(45) Date of Patent: *Jul. 1, 2014

(54) RIFAMYCIN DERIVATIVES

(71) Applicant: Alfa Wassermann, S.p.A., Alanno (PE) (IT)

(72) Inventors: Giuseppe Glaudio Viscomi, Bologna (IT); Manuela Campana, Bologna (IT); Mahena Folegatti, Bologna (IT); Paolo Righi, Bologna (IT); Vincenzo Cannata, Bologna (IT); Goffredo Rosini, Bologna (IT)

(73) Assignee: Alfa Wassermann S.p.A. (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/684,803

(22) Filed: Nov. 26, 2012

(65) Prior Publication Data

US 2013/0287692 A1    Oct. 31, 2013

Related U.S. Application Data

(63) Continuation of application No. 12/473,260, filed on May 27, 2009, now Pat. No. 8,318,763.

(30) Foreign Application Priority Data

Apr. 20, 2009  (IT) .................................. MI09A0653

(51) Int. Cl.
*A61K 31/395*    (2006.01)
(52) U.S. Cl.
USPC ......................................................... 514/279
(58) Field of Classification Search
USPC .......................................... 514/279; 540/456
See application file for complete search history.

(56) References Cited

PUBLICATIONS

Stradi R. et al., "Structural elucidation of the Rifaximin Ph. Eur. Impurity H", Oct. 28, 2009, pp. 858-865, 51, Journal of Pharmaceutical and Biomedical Analysis.
Rifaximin, Jan. 1, 2009, pp. 4955-4957, European Pharmacopoeia 6.5.
Rifaximin, Jan. 1, 2011, pp. 3459-3460, European Pharmacopoeia 7.1.

*Primary Examiner* — Bruck Kifle
(74) *Attorney, Agent, or Firm* — Steinfl & Bruno LLP

(57) ABSTRACT

Disclosed are rifamycin derivatives having antibacterial activities, wherein the compounds have the following general formula:

wherein:
R is hydrogen or acetyl; $R_1$ and $R_2$ are independently selected from the group consisting of hydrogen, ($C_{1-4}$) alkyl, benzyloxy, mono- and di-($C_{1-3}$) alkylamino-($C_{1-4}$)alkyl, ($C_{1-3}$) alkoxy, ($C_{1-4}$) alkyl, hydroxy-methyl, hydroxy-($C_{2-4}$)-alkyl, and nitro or $R_1$ and $R_2$ taken together with two consecutive carbon atoms of the pyridine nucleus form a benzene ring optionally substituted by one or two methyl or ethyl groups and $R_3$ is hydroxyalkyl ($C_{1-4}$). In addition, processes to obtain these compounds are described.

29 Claims, 7 Drawing Sheets

RIFAMYCIN DERIVATIVES

CROSS REFERENCE TO RELATED APPLICATIONS

This application is a continuation of U.S. patent application Ser. No. 12/473,260 filed on May 27, 2009, issued as U.S. Pat. No. 8,318,763 on Nov. 27, 2012, which claims priority to the Italian Patent Application Serial No. IT MI 2009 A 000653, filed on Apr. 20, 2009. The complete disclosure of each above-identified application is hereby fully incorporated herein by reference.

FIELD OF THE INVENTION

The present invention is in the field of pharmaceutical compositions, and particularly in the field of oral formulations for the treatment of inflammatory bowel disease.

BACKGROUND OF THE DISCLOSURE

Rifaximin (INN; see The Merck Index, XIII Ed., 8304), an antibiotic belonging to the rifamycin class, is a pyrido-imidazo rifamycin described and claimed in Italian Patent IT 1154655. European Patent EP 0161534 describes a process for its production starting from rifamycin O (The Merck Index, XIII Ed., 8301). Methods for making polymorphic forms of rifaximin are described in U.S. Patent Application Publication 2008-0262232, by Viscomi et al., which is incorporated by reference herein in its entirety.

Rifaximin has been used for treating acute and chronic intestinal infections from gram-positive and gram-negative bacteria and as adjuvant in the therapy of the hyperammonoaemia. Rifaximin is marketed in the United States as XIFAXAN™ for the treatment of travelers' diarrhea caused by the noninvasive strains of *Escherichia coli*. Rifaximin has also been used to treat *Clostridum difficile*-associated diarrhea, Crohn's disease, diverticular disease, hepatic encephalopathy, *Helicobacter pylori* eradication, infectious diarrhea, irritable bowel syndrome, pouchitis, prophylaxis for GI surgery, small bowel overgrowth, traveler's diarrhea and ulcerative colitis. Rifamycin derivatives bearing a heterocyclic ring condensed at the 3,4-position are known in the art. For example, U.S. Pat. Nos. 4,263,404 and 4,341,785 describe rifamycin and imidazo-rifamycin derivatives. Rifamycins have antibacterial activity and they are obtained from secondary metabolites of micro-organism cultures, useful in the treatment of infections, in particular in the tuberculosis as described by Sensi P. in Farmaco [Sci], (1959); 14:146-7 and by Mitnick C. D. et al. in Expert Opin. Pharmacother. (2009); 10:381-401. Recently the rifamycin derivatives have been identified as activators of the receptor X of pregnane (PRX), a member of the family of the nuclear receptor that regulates the metabolic enzyme expression involved in the mammalian response to chemical stimulation, as described Natl. Acad. Sci. USA, (1998), 95: 12208-12213.

Rifamycins are characterized by a chemical structure constituted from one or more condensed aromatic rings, forming a cyclic structure with an aliphatic ring as described by Prelong, V. et al. in Helv. Chim. Acta (1973); 56:2279. Rifamycin analogues are obtained by a chemical modification of the aromatic or aliphatic portions of the molecule, as described by Sensi P. in Research Progress in Organic Biological and Medicinal Chemistry (1964), 1, 337-421.

SUMMARY OF THE INVENTION

Disclosed herein is a compound of Formula

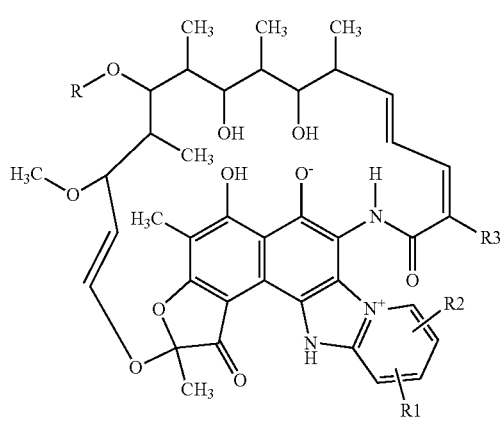

where:
R is hydrogen or acetyl,
$R_1$ and $R_2$ are each independently selected from the group consisting of hydrogen, $(C_{1-4})$alkyl, benzyloxy, mono- or di-$(C_{1-3})$alkylamino$(C_{1-4})$alkyl, $(C_{1-3})$ alkoxy-$(C_{1-4})$alkyl, hydroxy-methyl, hydroxy-$(C_{2-4})$-alkyl, and nitro; or $R_1$ and $R_2$ taken together with two consecutive carbon atoms of the pyridine ring form a benzene ring unsubstituted, or mono- or di-substituted by one or two methyl or ethyl groups; and
$R_3$ is hydroxyalkyl $(C_{1-4})$.

In some embodiments, R is an acetyl group, $R_1$ and $R_2$ are independently hydrogen or methyl, and $R_3$ is hydroxyalkyl $(C_{1-4})$. In other embodiments, R is an acetyl group, $R_1$ is hydrogen, $R_2$ is methyl and $R_3$ is hydroxymethyl.

In another aspect, disclosed herein is a process for the production of a compound of Formula II, the process comprising:

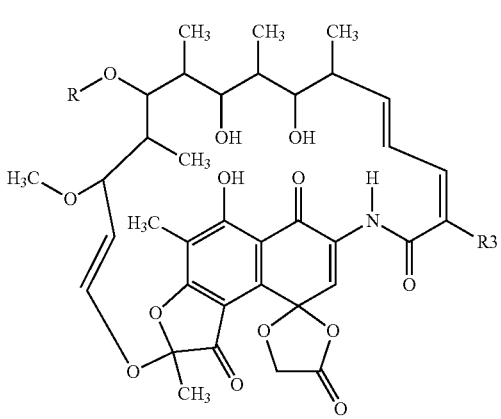

obtaining a biological culture comprising a microorganism in water solution, suitable for the production of rifamycin B derivatives, and nutritional agents; and
oxidizing the obtained culture with an oxidizing agent;
wherein R is hydrogen or acetyl, and $R_3$ is hydroxyalkyl $(C_{1-4})$.

In some embodiments, the oxidizing agent is selected from one or more of sodium nitrite, aqueous solution of potassium dichromate, ammonium persulphate, or sodium periodate. In certain embodiments, R is hydrogen or acetyl and $R_3$ is hydroxyalkyl ($C_{1-4}$). In further embodiments, R is acetyl and $R_3$ is hydroxymethyl.

In another aspect, disclosed herein is a process for synthesizing a compound of claim 1, comprising reacting a compound of Formula II,

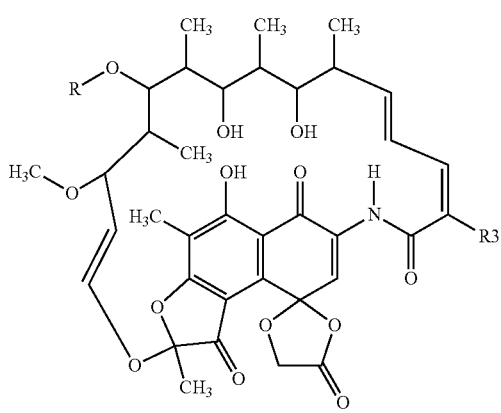

where R is hydrogen or acetyl, and $R_3$ is hydroxyalkyl ($C_{1-4}$), with a compound of Formula III:

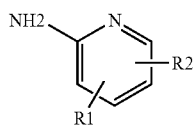

where $R_1$ and $R_2$ are each independently selected from the group consisting of hydrogen, ($C_{1-4}$)alkyl, benzyloxy, mono- or di-($C_{1-3}$)alkylamino($C_{1-4}$)alkyl, ($C_{1-3}$) alkoxy-($C_{1-4}$)alkyl, hydroxy-methyl, hydroxy-($C_{2-4}$)-alkyl, and nitro; or $R_1$ and $R_2$ taken together with two consecutive carbon atoms of the pyridine ring form a benzene ring unsubstituted, or mono- or di-substituted by one or two methyl or ethyl groups, in the presence of an organic solvent, a mixture of more than one organic solvents, or a mixture of an organic solvent with water, at a temperature between ambient temperature and 60° C., for a time between 1 and 100 hours.

In some embodiments, the organic solvent is selected from the group consisting of aromatic hydrocarbons, aliphatic alkanol, halogenated hydrocarbons, lower alkyl ester of lower aliphatic acid, glycols, acetonitril, dioxane, tetrahydrifurane, and a combination thereof, or in a mixture with water in different volumetric ratio. In certain embodiments, for each molar equivalent of compound of Formula II, from about 0.1 to about 1 molar equivalents of iodine or a combination of iodine/oxidizing agent is used. In further embodiments, the compound of Formula III is 2-amino-4-methyl-pyridine.

In another aspect, disclosed herein is a process for synthesizing a compound of claim 1, comprising: obtaining a biological culture comprising a microorganism suitable for the production of rifamycin B derivatives, in water solution, and nutritional agents; oxidizing the obtained culture with an oxidizing agent to obtain an oxidized product; and reacting the oxidized product with a 2-amino-pyridine derivative.

In yet another aspect, disclosed herein is a pharmaceutical composition comprising a therapeutically effect amount of a compound of Formula I in combination with one or more pharmaceutically acceptable ingredients. In some embodiments, the pharmaceutical composition is useful as an antibacterial.

In a further aspect, disclosed herein is a pharmaceutical composition comprising one or more compound of Formula I, or one or more compound of Formula I in combination with one or more compound of Formula II, and a pharmaceutically acceptable excipient. In some embodiments, the composition is administered in a single dosage form, whereas in other embodiments, the composition is administered in separate dosage forms. In other embodiments, the pharmaceutical composition further comprises a rifamycin derivative or neomycin. In some embodiments, the rifamycin derivative is rifaximin. In certain embodiments, the compound of Formula I is in a ratio from about 0.01 to 100% (w/w) with respect to rifaximin.

In another aspect, disclosed herein is a method of treating, preventing or alleviating bacterial overgrowth in a patient suffering from a bowel related disorder, comprising: identifying a subject in need thereof, and administering to the subject an effective amount of one or more compounds of Formula I in combination with one or more additional antibiotics. In some embodiments, the one or more additional antibiotics comprise one or more of rifamycin, rifaximin, or neomycin. In certain embodiments, the bowel related disorder is one or more of irritable bowel syndrome, travelers' diarrhea, small intestinal bacterial overgrowth, Crohn's disease, chronic pancreatitis, pancreatic insufficiency, hepatic encephalopathy, diverticulitis, enteritis, or colitis.

In yet another aspect, disclosed herein is a method of assessing the efficacy of a bowel related disorder treatment which reduces bacterial overgrowth, monitoring the progress of a subject being treated for a bowel related disorder, or selecting a subject for treatment of a bowel disorder, comprising: determining a pre-treatment level of bacterial overgrowth in a subject suffering from a bowel related disorder due to bacterial overgrowth; administering a therapeutically effective amount of a compound of Formula I in combination with rifaximin to the subject; determining a post-treatment level of bacterial overgrowth in the subject after an initial period of treatment; and determining the change in the level of bacterial overgrowth in the subject between the pre-treatment and post-treatment measurements. In some embodiments, the change in the level of bacterial overgrowth indicates efficacy of the treatment; wherein a decrease in the level of bacterial overgrowth indicates that the treatment is efficacious; or wherein the change in the level of bacterial overgrowth is an indication that the subject is likely to have a favorable clinical response to the treatment.

DETAILED DESCRIPTION OF THE EMBODIMENTS

Figure 1:
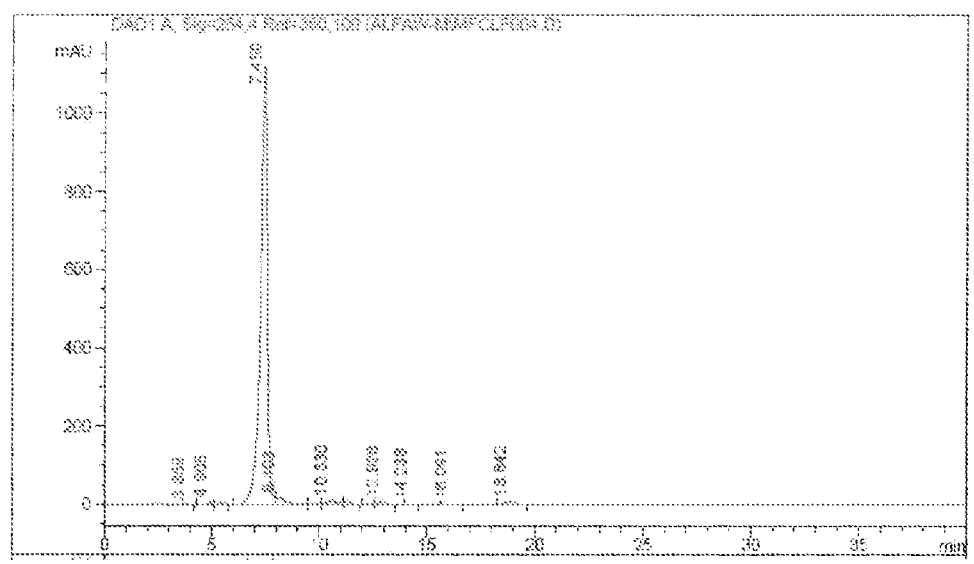
FIG. 1 shows the HPLC chromatogram of the compound of Formula II wherein R is acetyl and $R_3$ is hydroxymethyl.

In one aspect, disclosed herein are rifamycin derivatives of Formula I:

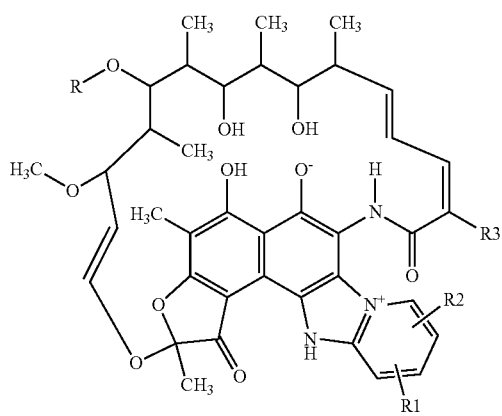

wherein:

R is hydrogen or acetyl;

$R_1$ and $R_2$ is each independently selected from the group consisting of hydrogen, $(C_{1-4})$ alkyl, benzyloxy, mono- and di-$(C_{1-3})$ alkylamino-$(C_{1-4})$ alkyl, $(C_{1-3})$ alkoxy, $(C_{1-4})$ alkyl, hydroxy-methyl, hydroxy-$(C_{2-4})$ alkyl, and nitro; or $R_1$ and $R_2$ taken together with two consecutive carbon atoms of the pyridine ring form a benzene ring, wherein the benzene ring is unsubstituted, mono-substituted, or di-substituted by methyl or ethyl; and $R_3$ is a $(C_{1-4})$ hydroxyalkyl.

In one embodiment of the compounds of Formula I, R is a hydrogen or an acetyl, $R_1$ and $R_2$ is each independently selected from the group consisting of hydrogen, $(C_{1-4})$ alkyl, benzyloxy, hydroxy $(C_{2-4})$ alkyl, and di-$(C_{1-3})$ alkylamino-$(C_{1-4})$ alkyl, or $R_1$ and $R_2$ taken together with two consecutive carbon atoms of the pyridine ring form a benzene ring, and $R_3$ is a $(C_{1-4})$ hydroxyalkyl.

Another embodiment comprises compounds of Formula I, wherein R is acetyl, $R_1$ and $R_2$ is each independently hydrogen or $(C_{1-4})$ alkyl, or $R_1$ and $R_2$ taken together with two consecutive carbon atoms of pyridine ring form a benzene ring, and $R_3$ is a $(C_{1-4})$ linear hydroxyalkyl.

As used herein the terms $(C_{1-3})$ alkyl, $(C_{2-4})$ alkyl and $(C_{1-4})$ alkyl identify linear or branched alkyl radicals containing from 1 to 3 or 2 to 4 or 1 to 4 carbon atoms, respectively, such as, for instance, methyl, ethyl, n-propyl, isopropyl, n-butyl, sec-butyl, isobutyl or ter-butyl, whereas the term $(C_{1-3})$ alkoxy essentially refers to methoxy, ethoxy, propoxy or isopropoxy groups.

The compounds presented herein may be prepared according to methods which depend on the type of compounds that are desired to be obtained. Thus, for instance, the compounds of Formula I wherein R and $R_3$ are as defined above, may be prepared by reacting compounds of Formula II, obtained as an intermediate product in a process analogous to the process described in U.S. Pat. No. 4,263,404, with an unsubstituted or substituted 2-amino-pyrridine compounds of formula III, as defined below:

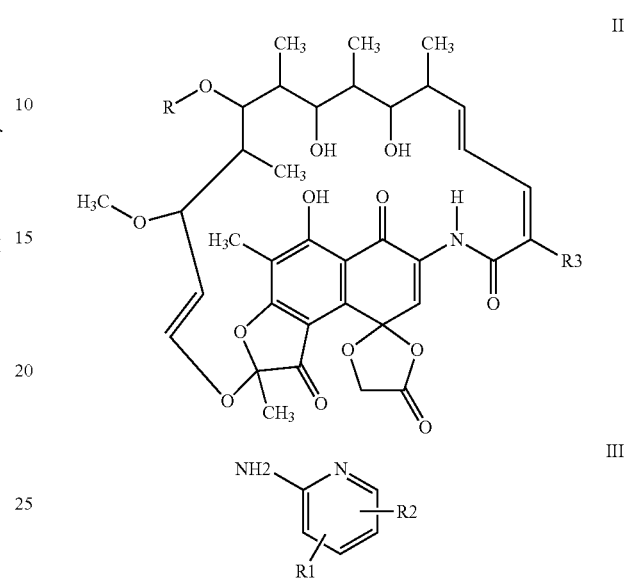

wherein $R_1$, $R_2$ and $R_3$ have the same meaning as above.

Compounds of Formula II may be obtained from a suitable biological culture of microorganisms such as *Streptomyces mediterranei* or *Nocardia mediterranea* in the presence of an oxidizing agent, such as sodium nitrite, potassium dichromate, ammonium persulfate, sodium periodate. Generally, the compounds of Formula II, and particularly when R is acetyl and $R_3$ is hydroxymethyl, can be obtained through purification processes of the mixture obtained from the above biological culture. The purification techniques can be, for instance, chromatography, crystallization, and organic solvent extraction. The analytical techniques useful to identify and to characterize the obtained compounds are $^1$H-NMR, IR spectroscopy, EIMS spectrometry, and chromatography (HPLC). The obtained compounds of Formula II can react with a molar excess of a selected amino-pyridine derivate of Formula III in a suitable solvent system from which, by means of techniques known to a person skilled in the art, the desired end product compounds of Formula I are recovered. The molar excess varies from about 2 to about 8 or more equivalents calculated based on the compound of Formula II.

The reaction may be carried out, for example, in the presence of a solvent or a solvent system, which is generally selected among those commonly used in rifamycin chemistry. For instance, aromatic hydrocarbons such as benzene or toluene, lower halogenated hydrocarbons, such as methylene chloride, chloroform, 1,2-dichloro-ethane and similar, lower alkanols, such as methanol, ethanol, propanol, isopropanol or n-butanol, may be used. Lower alkyl esters of lower aliphatic acid, glycols, acetonitrile, dioxane and tetrahydrofuran can also be conveniently employed. These solvents can be used alone, or in a mixture comprising two or more of the above solvents, or also in a mixture with water, in a different volumetric ratio. Preferable solvents include benzene, toluene, the lower halogenated hydrocarbons, the lower alkanols alone or in a mixture with water, acetonitrile, glycols, dioxane and tetrahydrofuran, used alone or in combination, or in a mixture with water.

The reaction may take place at ambient pressure and within a wide range of temperatures, for instance between room temperature and boiling temperature of the reaction mixture. Temperature ranges between room temperature, e.g., 20° C., and about 60° C. were found to be useful for preparing the compounds described herein. The reaction was completed in a period of time that varied depending on the nature of the aminopyridine substrate of Formula III and on the condition in which the reaction was carried out. Generally, from about 1 to about 100 hours were required to obtain the end products of Formula I with the desired yields. It was found that the reaction course can be favored if the reaction itself is carried out in presence of iodine or an appropriate iodine/oxidizing agent; wherein the iodine can be, for instance, the iodine of an alkali or an alkaline-earth metal and the hydroiodine of the same starting pyridine derivate and the oxidizing agent can be an agent capable of oxidizing, under the reaction conditions, the iodine ion, in order to release iodine in the reaction mixture. The iodine, or the iodine/oxidizing agent, can be present in the reaction mixture respectively in amounts from about 0.1 to about 1 molar equivalent of iodine, for each mole of starting compound represented in Formula II. In such a case, however, the reaction solution may be subsequently treated with a suitable reducing agent, for instance, ascorbic acid, isoascorbic acid or dihydroxiacetone.

The obtained compounds may undergo further chemical reactions to prepare other compounds of Formula I. Thus for instance, a compound of Formula I may be obtained, where R, $R_1$, $R_2$ and $R_3$ are as defined above, by treating the obtained compound with a suitable reducing agent such as, for instance, L (-) ascorbic acid.

The compounds of Formula I wherein R is hydrogen may be prepared by hydrolyzing, under alkaline conditions, the corresponding compound where R is acetyl.

The compounds presented herein may be recovered from the reaction medium, for example, by techniques familiar to a skilled technician. These techniques comprise the extraction with a suitable organic solvent, e.g., ethyl acetate, chloroform, methylene chloride and analogues or mixture thereof, the evaporation to dryness of the organic extract and taking up the residue with an appropriate solvent from which the final product separates. Alternatively the mixture can be directly evaporated to dryness and the obtained residue is in turn taken up with a suitable solvent from which the final product separates or crystallization or chromatography. The solvents which can advantageously be employed are selected from water, methanol, ethanol, n-propanol, isopropanol, n-hexane, ethylacetate, methylene chloroform, ethylene glycol monomethyl ether or a mixture thereof.

The compounds presented herein may be obtained, for example, with a purity higher than 90% from the reaction product by purification techniques known in the art, such as chromatography.

The compounds presented herein are useful antibacterial agents. They have in vitro activity both against Gram-positive and Gram-negative bacteria. The compounds have antibacterial affects on bacteria isolated from clinical samples, which can be found in the intestinal bacterial flora in pathologic conditions.

The anti-bacterial activity of compounds of Formula I was demonstrated by measuring the minimum concentration of active substance capable of inhibiting the growth in vitro of the pathogenic bacterium (MIC). They are expressed as milligrams of substance per liter of culture medium.

The anti-bacterial activity with one of the more representative compounds, where R is acetyl group, $R_1$ and $R_2$ are independently hydrogen or methyl group and $R_3$ is hydroxymethyl was measured in a large number of bacterial strains, belonging to different families such as Enterobacteriaceae, non-Enterobacteriaceae gram-negative, *Staphylococcus*. The MIC values are between from 0.06 to 128 mg/l and these values demonstrate the antibacterial efficacy of compound of Formula I.

In another embodiment, the compounds presented herein can be used as antibacterial agents, including their incorporation into pharmaceutical compositions. These compounds can be used alone or in combination with other antibiotics, such as rifampicin, rifamycin, neomycin and/or rifaximin, and in a broad range of ratio in weight, preferably from 0.01 to 100% by weight.

In another embodiment, the pharmaceutical preparation comprises compounds of Formula I with a pharmaceutically acceptable carrier, diluent, or excipient.

The compounds presented herein can therefore be administered by several routes, for example by oral, topical or parenteral route. For such administrations, the substances are embodied into conventional pharmaceutical dosage formulations. These formulations may contain compounds of Formula I alone or in a mixture compound of Formula II or other pharmaceutical active ingredient with the usual additives such as, for instance, sweetening, the usual additive such as, for instance, sweetening, flavoring, coloring, coating and preservative agents, inert diluents such as, for instance, calcium or sodium carbonate, lactose and talc, binding agents, e.g. starch, gelatine and polyvinylpyrrolidone, suspending agents, e.g. methylcellulose or hydroxyethycellulose, and wetting agents such as, for instance, lecithin, polyoxyethylene steatates and polyoxymethylene sorbitan monooleate.

The preparations useful for the topical and parenteral administration may contain the active ingredients dissolved or suspended in distilled and pyrogen-free water, in admixture with the commonly employed pharmaceutical carriers.

Another embodiment of the present invention is the use of a compound of Formula I alone, or in a combination with another compound of Formula I, or in combination with a compound of Formula II, or in combination with other pharmaceutically active agents to treat or to prevent the bacterial infections. In particular, the presently disclosed pharmaceutical compositions can be used to treat a patient suffering from a bowel related disorder, including, but not limited to, one or more of irritable bowel syndrome, diarrhea, microbe associated diarrhea, *Clostridium difficile*-associated diarrhea, travelers' diarrhea, small intestinal bacterial overgrowth, Crohn's disease, chronic pancreatitis, pancreatic insufficiency, colitis, hepatic encephalopathy, diverticulitis, and pouchitis.

Methods of Treatment

In one embodiment, the compounds disclosed herein possess antibacterial activity and have a role in activation of the pregnane X receptor (PRX), a nuclear receptor that regulates genes involved in xenobiotic and limited endobiotic deposition and detoxification.

Provided herein are methods of treating, preventing, or alleviating a bowel related disorders comprising administering to a subject in need thereof a therapeutically effective amount of one or more compounds disclosed herein. Bowel related disorders include one or more of irritable bowel syndrome, diarrhea, microbe associated diarrhea, *Clostridium difficile*-associated diarrhea, travelers' diarrhea, small intestinal bacterial overgrowth, Crohn's disease, chronic pancreatitis, pancreatic insufficiency, colitis, hepatic encephalopathy, diverticulitis, and pouchitis.

The length of treatment for a particular bowel disorder will depend in part on the disorder. For example, travelers' diarrhea may only require treatment duration of 12 to about 72 hours, while Crohn's disease may require treatment durations from about 2 days to 3 months. Dosages will also vary depending on the diseases state. Proper dosage ranges are provided herein infra.

Provided herein are methods of treating or preventing a pathological condition in a patient suspected of being exposed to a biological warfare agent.

The identification of those patients who are in need of prophylactic treatment for bowel disorder is well within the ability and knowledge of one skilled in the art. Certain of the methods for identification of patients who are at risk of developing a bowel disorder that can be treated by the methods disclosed herein are appreciated in the medical arts, such as family history, travel history and expected travel plans, the presence of risk factors associated with the development of that disease state in the subject patient. A clinician skilled in the art can readily identify such candidate patients, by the use of, for example, clinical tests, physical examination and medical/family/travel history.

A method of assessing the efficacy of the treatment in a subject includes determining the pre-treatment level of intestinal bacterial overgrowth by methods well known in the art (e.g., hydrogen breath testing, biopsy, sampling of the intestinal bacteria, etc.) and then administering a therapeutically effective amount of compounds presented herein the subject. After an appropriate period of time (e.g., after an initial period of treatment) from the administration of the compound, e.g., 2 hours, 4 hours, 8 hours, 12 hours, or 72 hours, the level of bacterial overgrowth is determined again. The modulation of the bacterial level indicates efficacy of the treatment. The level of bacterial overgrowth may be determined periodically throughout treatment. For example, the bacterial overgrowth may be checked every few hours, days or weeks to assess the further efficacy of the treatment. A decrease in bacterial overgrowth indicates that the treatment is efficacious. The method described may be used to screen or select patients that may benefit from treatment with compounds presented herein. In yet another aspect, a method of treating a subject suffering from or susceptible to a bowel disorder comprises administering to a subject in need thereof a therapeutically effective amount of compounds presented herein, to thereby treat the subject. Upon identification of a subject suffering from or susceptible to a bowel disorder, for example, IBS, one or more compounds presented herein are administered.

In one aspect, methods of assessing the efficacy of treatment with a compound presented herein, or in a mixture with other active ingredients in a subject comprise determining the pre-treatment level of bacterial overgrowth, administering a therapeutically effective amount of the compound of Formula I or II, either alone or in a combination with other active ingredients, to the subject, and determining the bacterial overgrowth after an initial period of treatment with compounds presented herein, wherein the modulation of the bacterial overgrowth indicates efficacy of an anti-bacterial treatment.

Efficacy of a treatment may be measured for example, as reduction of bacterial overgrowth. Efficacy may also be measured in terms of a reduction of symptoms associated with the bowel disorder, a stabilization of symptoms, or a cessation of symptoms associated with a bowel disorder, for example, a reduction of nausea, bloating, diarrhea, and the like.

In one aspect, methods of monitoring the progress of a subject being treated with a compounds presented herein comprise determining the pre-treatment level of bacterial overgrowth, administering a therapeutically effective amount of a compound presented herein to the subject, and determining the bacterial overgrowth after an initial period of treatment with a compounds presented herein, wherein the modulation of the bacterial overgrowth indicates efficacy of an anti-bacterial treatment.

Pharmaceutical Preparations

Also provided herein are pharmaceutical compositions, comprising, for example, an effective amount of a rifamycin derivative alone or in association with other pharmaceutical active ingredients in a pharmaceutically acceptable carrier. In a further embodiment, the effective amount is effective to treat a bacterial infection, e.g., small intestinal bacterial overgrowth, Crohn's disease, hepatic encephalopathy, antibiotic associated colitis, and/or diverticular disease.

For examples of the use to treat Travelers' diarrhea, see Infante R M, Ericsson C D, Zhi-Dong J, Ke S, Steffen R, Riopel L, Sack D A, DuPont, H L. Enteroaggregative *Escherichia coli* Diarrhea in Travelers: Response to Rifaximin Therapy. *Clinical Gastroenterology and Hepatology*. 2004; 2:135-138; and Steffen R, M.D., Sack D A, M.D., Riopel L, Ph.D., Zhi-Dong J, Ph.D., Sturchler M, M.D., Ericsson C D, M.D., Lowe B, M. Phil., Waiyaki P, Ph.D., White M, Ph.D., DuPont H L, M.D. Therapy of Travelers' Diarrhea With Rifaximin on Various Continents. *The American Journal of Gastroenterology*. May 2003, Volume 98, Number 5, all of which are incorporated herein by reference in their entirety.

The pharmaceutical compositions may contain one or more compounds of Formulas I or II or may contain a mixture of more than one of the compounds represented by the same formula, or a mixture of compounds of Formula I with compounds of Formula II, or in a mixture with other pharmaceutically active ingredients. Mixtures may be selected, for example on the basis of desired amounts of systemic adsorption, dissolution profile, desired location in the digestive tract to be treated, and the like. The pharmaceutical compositions may further comprise carrier, for example, one or more of a diluting agent, binding agent, lubricating agent, disintegrating agent, colouring agent, flavouring agent or sweetening agent. Compositions may be formulated for selected coated and uncoated tablets, hard and soft gelatine capsules, sugar-coated pills, lozenges, wafer sheets, pellets and powders in sealed packet. For example, compositions may be formulated for topical use, for example, ointments, pomades, creams, gels and lotions.

In an embodiment, the rifamycin derivatives are administered to the subject using a pharmaceutically-acceptable formulation, e.g., a pharmaceutically-acceptable formulation that provides sustained delivery to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions presented herein may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compounds presented herein, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes a pharmaceutically-acceptable material, composition or vehicle, such as a liquid or solid filler, diluents, excipients, solvents or encapsulating material, involved in carrying or transporting the subject chemical from one organ, or portion of the body, to another organ, or portion of the body. Each carrier is preferably "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatine; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminium hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulphate and magnesium stearate, as well as colouring agents, release agents, coating agents, sweetening, flavouring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulphite, sodium sulphite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a rifamycin derivatives include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred %, this amount will range from about 1% to about ninety-nine % of active ingredient, preferably from about 5% to about 70%, most preferably from about 40% to about 70%.

Methods of preparing these compositions may include the step of bringing into association a rifamycin derivatives alone or in a mixture with other active ingredients with the carrier and, optionally, one or more accessory ingredients. In general, the formulations are prepared by uniformly and intimately bringing into association a rifamycin derivatives alone or in a mixture with other active ingredients with liquid carriers, or finely divided solid carriers, or both, and then, if necessary, shaping the product.

Compositions presented herein suitable for oral administration may be in the form of capsules, cachets, pills, tablets, lozenges (using a flavoured basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a rifamycin derivatives of Formula I alone or in a mixture with other active ingredients. A compound may also be administered as a bolus, electuary or paste.

The rifamycin derivative can be advantageously used in the production of medicinal preparations having antibiotic activity for both oral and topical use. The medicinal preparations for oral use may contain, together with the usual excipients, for example diluting agents such as mannitol, lactose and sorbitol; binding agents such as starches, gelatines, sugars, cellulose derivatives, natural gums and polyvinylpyrrolidone; lubricating agents such as talc, stearates, hydrogenated vegetable oils, polyethylenglycol and colloidal silicon dioxide; disintegrating agents such as starches, celluloses, alginates, gums and reticulated polymers; colouring, flavouring and sweetening agents.

The compounds presented herein include solid preparations administrable by the oral route, for instance coated and uncoated tablets, of soft and hard gelatine capsules, sugar-coated pills, lozenges, wafer sheets, pellets and powders in sealed packets or other containers.

The medicinal preparations for topical use may contain rifamycin derivatives of Formula I alone or in a mixture of them or in association with compounds of Formula II or in a mixture with other active ingredients, together with usual excipients, such as white petrolatum, white wax, lanoline and derivatives thereof, stearich alcohol, propylene glycol, sodium lauryl sulfate, ethers of fatty polyoxyethylene alcohols, esters of fatty polyoxyethylene acids, sorbitan monostearate, glyceryl monostearate, propylene glycol monostearate, polyethylene glycols, methylcellulose, hydroxymethyl propylcellulose, sodium carboxymethylcellulose, colloidal aluminium and magnesium silicate, sodium alginate.

The compounds presented herein may be prepared in various formulations, for example, topical preparations, for instance ointments, pomades, creams, gels and lotions.

In solid dosage forms presented herein for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such as talc, calcium stearate, magnesium stearate, solid polyethylene glycols, sodium lauryl sulphate, and mixtures thereof; and (10) colouring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or moulding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Moulded tablets may be made by moulding in a suitable machine a mixture of the powdered active ingredient moistened with an inert liquid diluent.

The tablets, and other solid dosage forms of the pharmaceutical compositions of compounds presented herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in microencapsulated form, if appropriate, with one or more of the above-described excipients.

Liquid dosage forms for oral administration of the rifamycin derivatives of Formula I alone or in a mixture of them or in association with compounds of Formula II or in a mixture with other active ingredients include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilising agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavouring, colouring, perfuming and preservative agents.

Suspensions, in addition to the active rifamycin derivates of Formula I alone or in a mixture of them or in association with compounds of Formula II or in a mixture with other active ingredients may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions presented herein for rectal or vaginal administration may be presented as a suppository, which may be prepared by mixing one or more rifamycin derivates alone or in a mixture of them or in association with compounds of Formula II or in a mixture with other active ingredients with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions presented herein which are suitable for vaginal administration also include pessaries, tampons, creams, gels, pastes, foams or spray formulations containing such carriers as are known in the art to be appropriate.

Dosage forms for the topical or transdermal administration of a rifamycin derivatives include powders, sprays, ointments, pastes, creams, lotions, gels, solutions, patches and inhalants. The active rifamycin derivatives may be mixed under sterile conditions with a pharmaceutically-acceptable carrier, and with any preservatives, buffers, or propellants which may be required.

The ointments, pastes, creams and gels may contain, in addition to rifamycin derivates presented herein, excipients, such as animal and vegetable fats, oils, waxes, paraffin, starch, tragacanth, cellulose derivatives, polyethylene glycols, silicones, bentonites, silicic acid, talc and zinc oxide, or mixtures thereof.

Powders and sprays can contain, in addition to a rifamycin derivatives alone or in a mixture of them or in association with compounds of Formula II or in a mixture with other active ingredients, excipients such as lactose, talc, silicic acid, aluminium hydroxide, calcium silicates and polyamide powder, or mixtures of these substances. Sprays can additionally contain customary propellants, such as chlorofluorohydrocarbons and volatile un-substituted hydrocarbons, such as butane and propane.

The rifamycin derivatives alone or in a mixture of them or in association with compounds of Formula II or in a mixture with other active ingredients can be alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a rifamycin derivatives alone or in a mixture of them or in association with compounds of Formula II or in a mixture with other active ingredients to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope presented herein.

Pharmaceutical compositions presented herein suitable for parenteral administration comprise one or more rifamycin derivatives alone or in a mixture of them or in association with compounds of Formula II or in a mixture with other active ingredients in combination with one or more pharmaceutically-acceptable sterile isotonic aqueous or no aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions presented herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, to prolong the effect of a drug, it is desirable to slow the absorption of the drug from subcutaneous or intramuscular injection. Injectable depot forms are made by forming microencapsule matrices of rifamycin derivatives alone or in a mixture of them or in association with compounds of Formula II or in a mixture with other active ingredients in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the rifamycin derivatives of Formula I alone or in a mixture of them or in association with compounds of Formula II or in a mixture with other active ingredients are administered as pharmaceuticals to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the rifamycin derivatives of Formula I alone or I a mixture of them or in association with compounds of Formula II or in a mixture with other active ingredients, which may be used in a suitable hydrated form, and/or the pharmaceutical compositions presented herein, are formulated into pharmaceutically-acceptable dosage forms by conventional methods known to those of skill in the art.

Actual dosage levels and time course of administration of the active ingredients in the pharmaceutical compositions presented herein may be varied so as to obtain an amount of the active ingredient which is effective to achieve the desired therapeutic response for a particular patient, composition, and mode of administration, without being toxic to the patient. An exemplary dose range is from 1 to 3000 mg per day.

A preferred dose of the rifamycin derivatives of Formula I presented herein is the maximum that a patient can tolerate without developing serious side effects. In one embodiment, the rifamycin derivatives presented herein are administered at a concentration of about 1 mg to about 200 mg per kilogram of body weight, about 10-about 100 mg/kg or about 40 mg-about 80 mg/kg of body weight. Ranges intermediate to the above-recited values are also within the scope of the invention.

In combination therapy treatment, both the compounds presented herein and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment presented herein in which another therapeutic agent is administered to an animal, the effective amount of the compound presented herein is less than its effective amount in case the other therapeutic agent is not administered. In another embodiment, the effective amount of the conventional agent is less than its effective amount in case the presented herein are not administered. In this way, undesired side effects associated with high doses of either agent may be minimized. Other potential advantages (including without limitation improved dosing regimens and/or reduced drug cost) will be apparent to those skilled in the art.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patient's visit.

In certain embodiments, one or more compounds presented herein and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the administration of the same compounds presented herein may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than a rifamycin derivatives may be repeated and the administration may be separated by at least at least 1 day, 2 days, 3 days, 5 days, 10 days, 15 days, 30 days, 45 days, 2 months, 75 days, 3 months, or at least 6 months.

Certain indications may require longer treatment times. For example, travelers' diarrhea treatment may only last from between about 12 hours to about 72 hours, while a treatment for Crohn's disease may be from between about 1 day to about 3 months.

Kits are also provided herein, for example, kits for treating a bowel disorder in a subject. The kits may contain, for example, one or more of rifamycin derivatives alone or in a mixture of them or in association with compounds of Formula II or in a mixture with other active ingredients and instructions for use. The instructions for use may contain prescribing information, dosage information, storage information, and the like.

Packaged compositions are also provided, and may comprise a therapeutically effective amount of one or more of a rifamycin derivatives alone or in association with compounds of Formula II or in a mixture with other active ingredients and a pharmaceutically acceptable carrier or diluent, wherein the composition is formulated for treating a subject suffering from or susceptible to a bowel disorder, and packaged with instructions to treat a subject suffering from or susceptible to a bowel disorder.

EXAMPLES

Example 1

This example provides one method for making (12'Z,14'E, 24'E)-5',17',19'-trihydroxy-12'-(hydroxymethyl)-23'-methoxy-2'-,4',16',18',20',22'-hexamethyl-1',4,6'11'tetraoxo-1',2'-dihydro-6'H-spiro[-1,3-dioxolane-2,9'-[2,7]epoxypentadeca[1,11,13]trienoimino)naphto[2,1-b]furan]-21'-yl acetate. This compound is the compound of Formula II where R is acetyl and $R_3$ is hydroxymethyl.

A culture of *Nocardia mediterranea* (ATCC 31064) was propagated for 6-8 days on Benett's agar and incubated at 28° C. Two 500 ml Erlenmeyer flasks were inoculated, under sterile conditions, with the culture obtained from the agar slant. The flasks contained 100 ml of vegetative medium composition as described in Table 1.

TABLE 1

| Component | Quantity |
| --- | --- |
| Beef extract | 5 g |
| Yeast extract | 5 g |
| Peptone | 5 g |
| Casein hydrolyzate | 3 g |
| Glucose | 20 g |
| NaCl | 1.5 g |
| $H_2O$ | 1 liter |

The pH was adjusted to 7.3 with 1M NaOH. The flasks so inoculated were placed on an alternative shaker at 28° C. for 72 hours. The content of the two Erlenmeyer flasks was used as inoculum by pouring it in a 10-liter pre-fermenter, containing 4 liters of the above mentioned vegetative medium. The incubation was carried out at 28° C. with an agitation of 300 r.p.m. and 1 v/v/m aeration. After 48 hours of growth a volume of 7-10% of packed cell was obtained.

In the next stage the cells were used as an inoculum in a 10 liter glass fermenter containing 4 liters of medium composition as described below and in Table 2:

TABLE 2

| Component | Quantity |
| --- | --- |
| Peanut flour | 25 g |
| Soybean flour | 5 g |
| $(NH4)_2SO_4$ | 9.5 g |
| $MgSO_4 \cdot 7H_2O$ | 0.85 g |
| Glucose | 95 g |
| Glycerol | 40 g |
| $KH_2PO_4$ | 1 g |
| Propylene glycol | 5 g |
| $CaCO_3$ | 8.5 g |
| Na diethylbarbiturate | 1.7 g |
| $CuSO_4 \cdot 5H_2O$ | 2.8 mg |
| $FeSO_4 \cdot 7H_2O$ | 8.5 mg |
| $ZnSO_4 \cdot 7H_2O$ | 42.5 mg |
| $MnSO_4 \cdot 7H_2O$ | 3.4 mg |
| $CaCl_2 \cdot 7H2O$ | 1.7 mg |
| $(NH_4)_6Mo_7O_{24} \cdot 4H_2O$ | 0.85 mg |
| $H_2O$ to | 1 litre |

The pH was adjusted to 7.8 with NaOH and sterilized for 60 minutes at 120° C. After sterilization the pH was 6.4. An amount of the prefermenter content equal to 5% of the fermenter content was used as an inoculum. The fermentation was carried out at 28° C. with a 750 r.p.m. agitation and aerating at a rate of 1/v/v/m. Silicone A was used as antifoam. The culture broth turned to a characteristic red-brown color during the fermentation. After about 200 hours of growth a volume of packed cells was obtained. The pH of the broth was 7.5, and the broth was then harvested to remove the cells.

The mycelium was removed by filtration and discarded. The filtrate was adjusted to pH 2.0 with 10% (v/v) hydrochloric acid and extracted three times with an equal volume of ethylacetate. The combined extracts were concentrated to dryness under vacuum at 35° C. and the residue was dissolved in 0.005 M sodium phosphate buffer pH 7.5. Sodium nitrite was added to give a final concentration of 0.2% (w/v). After stirring for 30 min. at room temperature the buffer solution was extracted three times with an equal volume of ethyl acetate. The combined organic extracts were concentrated to dryness under vacuum at 35° C. The extract was purified using silica gel column chromatography in isocratic condition of elution with a mixture of solvents dichloro methane/methanol in the ratio 40/1 (v/v), liner velocity of 2.65 cm/min, with a loading capacity of 1 gram of mixture to separate in 13 milliliters of stationary phase.

Figure 2:
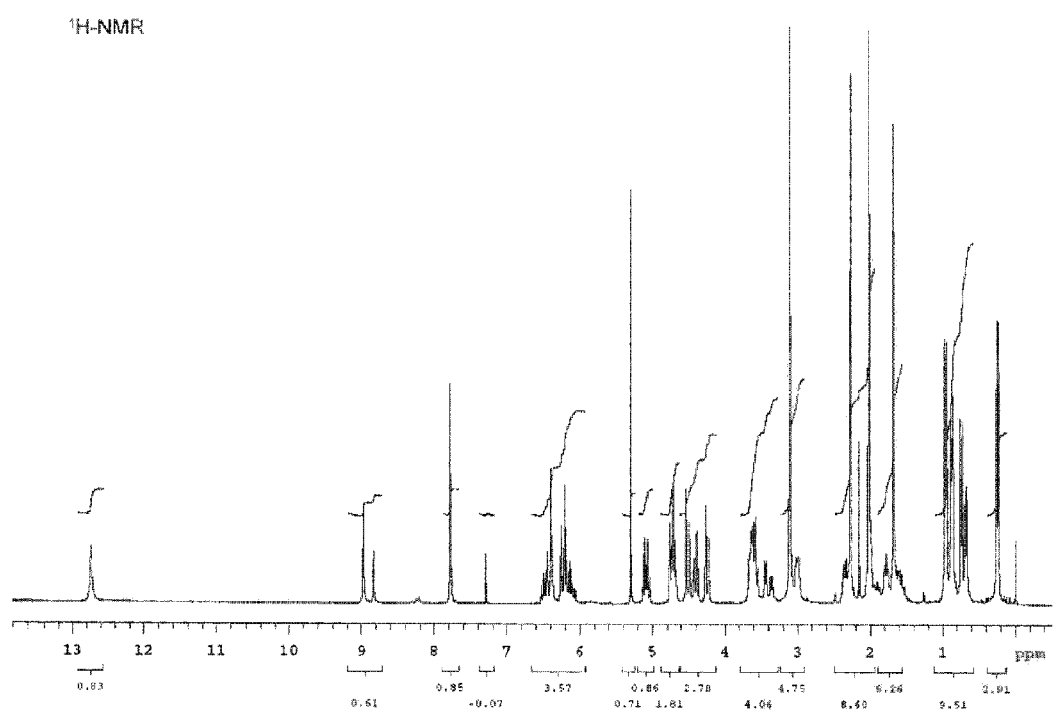
FIG. 2 shows the $^1$H NMR spectrum of the compound of Formula II wherein R is acetyl and $R_3$ is hydroxymethyl.

The obtained compound was analyzed in HPLC, using a Hypersil ODS column having dimensions of 250 mm of length and 4.4 mm of diameter, eluted in isocratic condition with acetonitrile/0.025 M Sodium Phosphate bi-acid pH 7.0 buffer, in the ratio 1/1 (v/v) with a flow rate of 1 ml/min. The chromatographic fraction with a purity higher than 90% were collected and the solvent concentrated to dryness under vacuum. The chromatographic profile of compound of Formula II wherein R is acetyl and $R_3$ is hydroxymethyl, characterized by a Retention Time (RT) of 7.45 min. is in FIG. 1. The compound was identified by $^1$H NMR and the spectrum is shown in FIG. 2.

Example 2

This example provides one method for producing 16Z, 18E,28E)-25-(acetyloxy)-5,21,23-trihydroxy-16-(hydroxymethyl)-27-methoxy-2,4,11,20,22,24,26-heptamethyl-1,15-dioxo-1,13-dihydro-2H-2,7-(epoxypentadeca[1,11,13]trienoimino)furo[2'',3'':7',8']naphto[1',2':4,5]imidazo[1,2-a]pyridine-8-ium-6-olate. This compound is the compound of Formula I, where R is acetyl, $R_1$ is hydrogen, $R_2$ is p-methyl and $R_3$ is hydroxymethyl.

A solution of 200 mg of (12'Z,14'E,24'E)-5',17',19'-trihydroxy-12'-(hydroxymethyl)-23'-methoxy-2',4',16',18',20',22'-hesamethyl-1',4,6'11'tetraoxo-1',2'-dihydro-6'H-spiro[1,3-dioxolane-2,9'-[2,7]epoxypentadeca[1,11,13]trienoimino)naphto[2,1-b]furan]-21'-yl acetate, obtained as described in Example 1, was dissolved in 0.6 ml distilled water and 0.5 ml ethanol were added under stirring at room temperature with 82 mg of 2-amino-4-methyl-pyridine. The reaction mixture was kept at 47° C. for about five hours until complete disappearance of the reagent of Formula II by HPLC analysis in the same reported in Example 1. The solution was brought to ambient temperature and 5 mg of ascorbic acid were added. The solution was acidified to pH 2.0 with concentrated HCL and than the solution was extracted with two aliquots of about 1.0 ml of ethylene acetate. The pooled organic phases were dried over sodium sulfate, filtered and evaporated by dryness.

Figure 3:
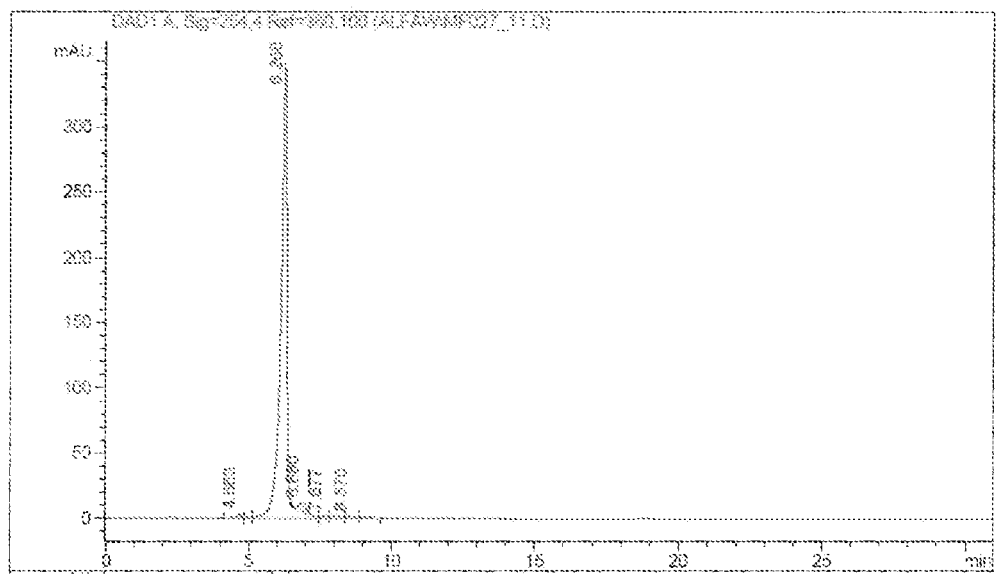
FIG. 3 shows the HPLC chromatogram of the compound of Formula I, wherein R is acetyl, $R_1$ is hydrogen, $R_2$ is methyl and $R_3$ is hydroxymethyl.

The obtained compound analyzed in HPLC under the same conditions of Example 1, is characterized by a RT of 6.2 min., with a purity corresponding to 95% and the chromatogram is in FIG. 3. The obtained compound was identified in FT-IR, $^1$H-NMR, $^{13}$C-NMR spectroscopy and the molecular weight determined with EIMS spectroscopy.

Figure 4:
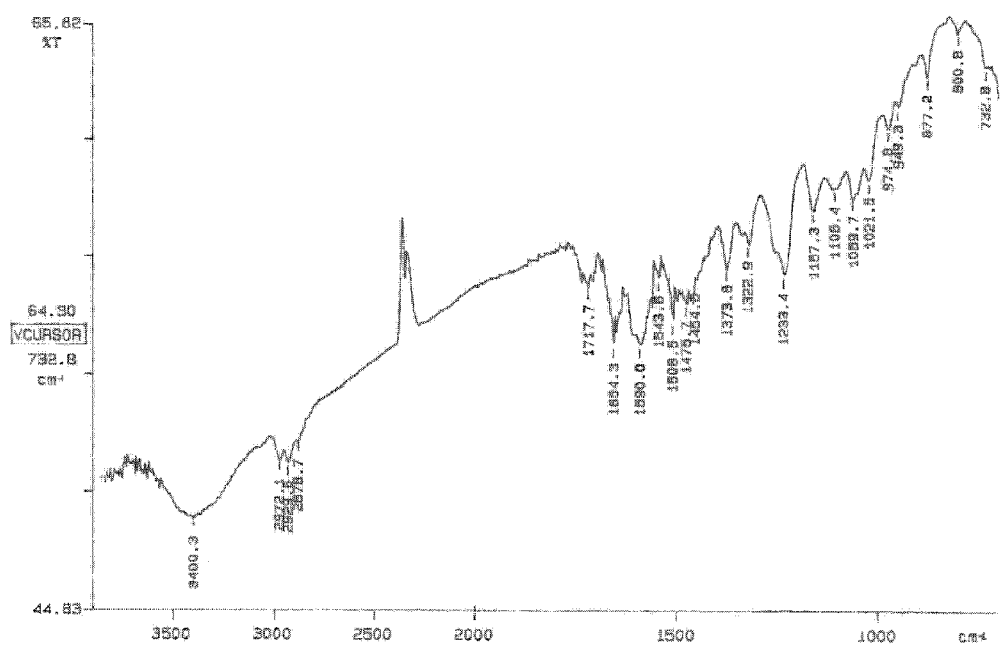
FIG. 4 shows the IR spectrum of the compound of Formula I, wherein R is acetyl, $R_1$ is hydrogen, $R_2$ is methyl and $R_3$ is hydroxymethyl.

I.R Spectrum—characteristic absorption bands were observed at the following frequencies (in $cm^{-1}$), obtained with a NaCl film: 3400, 2972, 2929.6, 1717.7, 1654.3, 1690.0, 1543.6, 1508.5, 1475.7, 1454.5, 1373.8, 1322.9, 1233.4, 1157.3, 1106.4, 1059.7, 1021.5, 974.8, 949.3, 877.2, 800.8, 732.8. The spectrum is shown in FIG. 4 and the data are in agreement with the proposed structures.

Figure 5:
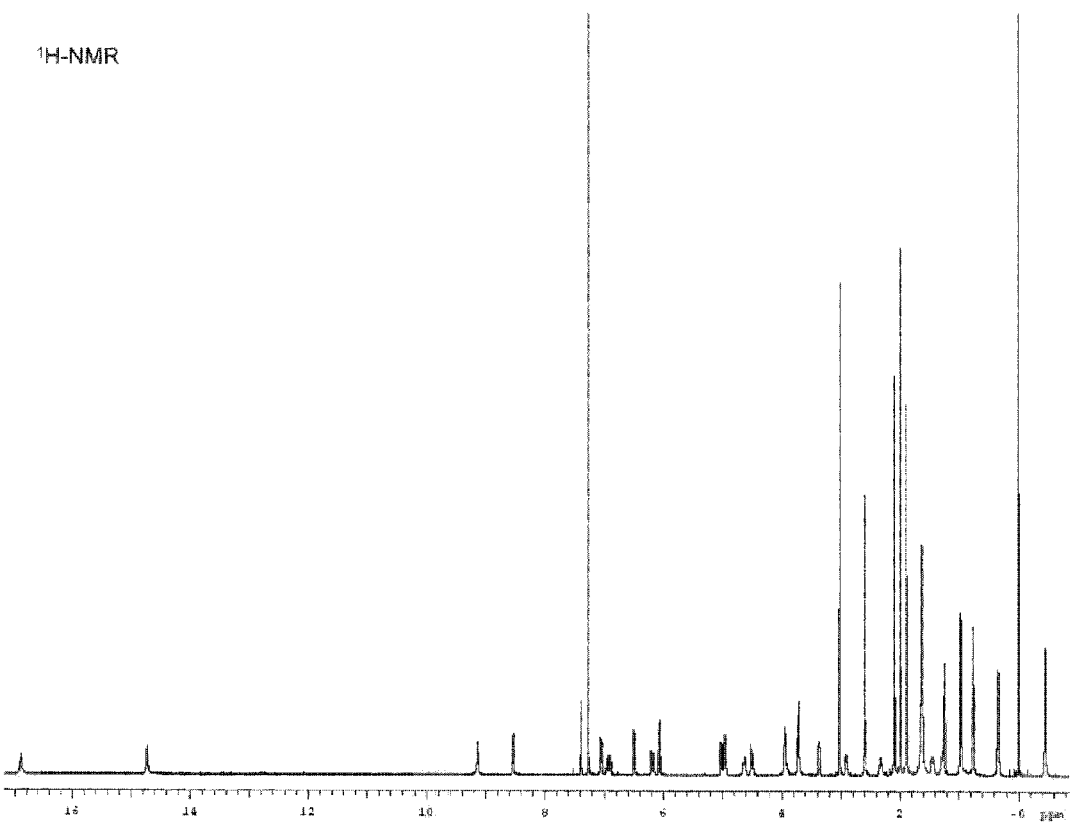
FIG. 5 shows the $^1$H NMR spectrum of the compound of Formula I wherein R is acetyl, $R_1$ is hydrogen, $R_2$ is methyl and $R_3$ is hydroxymethyl.

$^1$H-N.M.R. Spectrum—. Characteristic resonance peaks were observed at the following δ (expressed as p.p.m.): 0.34 (d, 3H), 0.76 (d, 3H), 0.97 (d, 3H), 1.27, (m, 1H) 1.44 (m, 1H), 1.63 (m, 1H), 1.89 (s, 3H), 1.99 (s, 3H), 2.09 (s, 3H), 2.32 (m, 1H), 2.59 (s, 3H), 2.91 (m, 1H), 3.02 (s, 3H), 3.37 (d, 1H), 3.73 (m, 2H), 3.95 (m, 2H), 4.50 (d, 1H), 4.63 (d, 1H), 4.95 (d, 1H), 5.01 (d, 1H), 6.06 (d, 1H), 6.18 (d, 1H), 6.49 (d, 1H), 6.92 (d, 1H), 7.05 (d, 1H), 7.39 (s, 1H), 8.53 (d, 1H), 9.13 (s, 1H), 14.73 (s, 1H), 16.89 (s, 1H), where s=singlet, d=doublet, m=multiplet. The spectrum is shown in FIG. 5 and the data are in agreement with the proposed structure.

Figure 6:
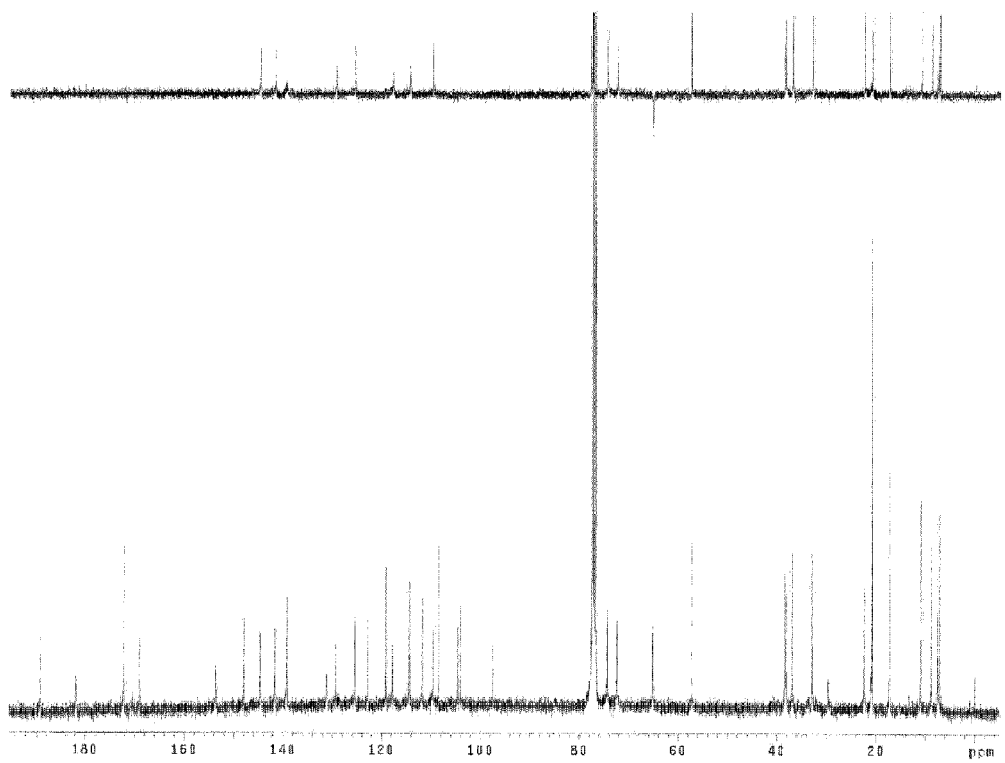
FIG. 6 shows the $^{13}C$ NMR spectrum of the compound/ obtained of Formula I, wherein R is acetyl group, $R_1$ is hydrogen, $R_2$ is methyl and $R_3$ is hydroxymethyl.

$^{13}$C-N.M.R. Spectrum—. Characteristic resonance peaks were observed at the following δ (expressed as p.p.m.): 7.14, 7.47, 8.75, 10.90, 17.25, 20.79, 22.33, 32.81, 36.87, 38.14, 38.35, 57.24, 65.13, 72.35, 74.31, 77.16, 77.62, 97.51, 103.98, 104.53, 108.43, 109.58, 111.77, 114.29, 114.29, 114.37, 117.74, 119.09, 122.77, 125.39, 129.26, 139.09, 139.28, 141.15, 144.54, 147.93, 153.59, 169.05, 172.08, 172.14, 181.82, 189.19. The spectrum is shown in FIG. 6 and the data are in agreement with the proposed structure.

Figure 7:
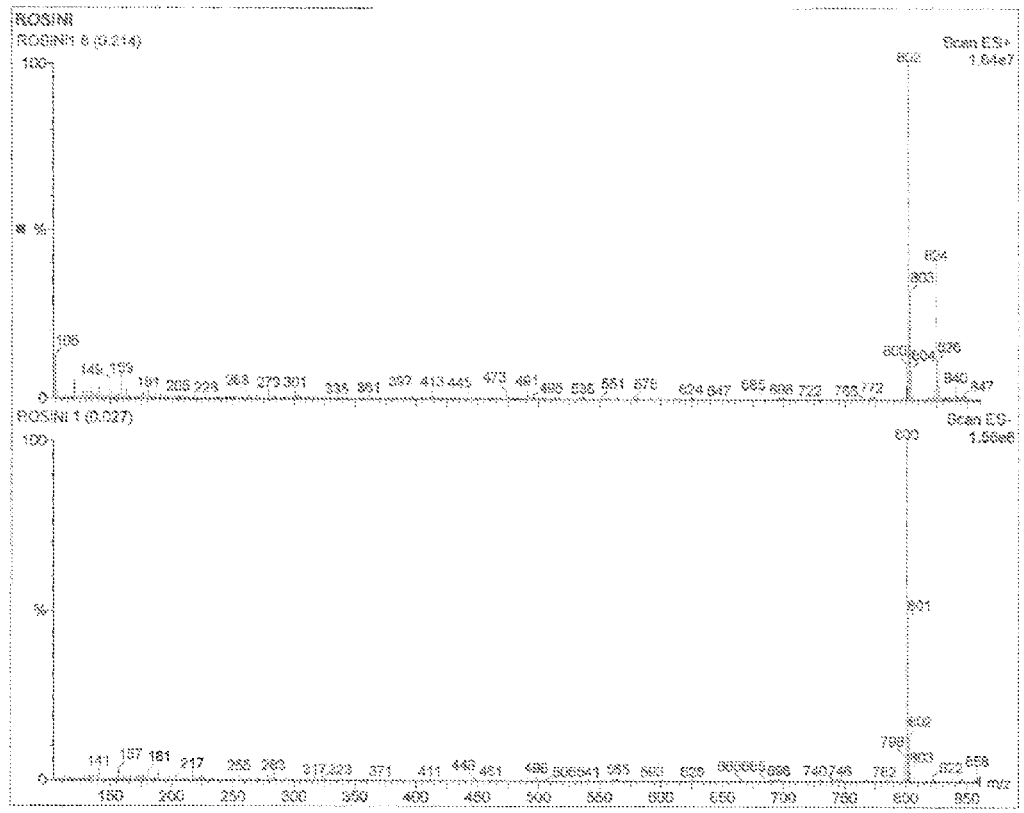
FIG. 7 shows the EIMS spectrum of the compound of Formula I, wherein R is acetyl group, $R_1$ is hydrogen, $R_2$ is methyl and $R_3$ is hydroxymethyl.

EIMS: The molecular weight was determinate with tuning parameter ESI+ and ESI−, with a capillary 3.00 KV, a cone of 25V and an extractor of 3 KV. The spectrum is in FIG. 7 and the obtained compound had a molecular weight corresponding to 801.

Example 3

The minimum concentration of the active substance capable of inhibiting the growth in vitro of the pathogenic bacterium (MIC) was determined with the micro dilution method as described in National Committee for Clinical Laboratory Standards NCCLS, 2003 and E. coli (ATCC 25922), P. aeruginosa (ATCC 27853), S. aureus (ATCC 29213), E. faecalis (ATCC 29212) were inserted as a control standard.

Table 3 reports the results of the minimum concentration of inhibition the growth in vitro on different strains of gram-negative bacteria.

Table 4 reports the results of the minimum concentration of inhibition the growth in vitro on different strains of Staphylococcus spp and Enterococus spp.

TABLE 3

| Number | Strain | MIC (mg/L) |
| --- | --- | --- |
| 92 | C. freundii | 128 |
| 94 | C. freundii | 128 |
| 99 | C. freundii | 128 |
| 106 | C. freundii | 128 |
| 109 | C. freundii | 128 |
| 89 | C. freundii | 128 |
| 93 | C. freundii | 128 |
| 95 | C. freundii | 128 |
| 96 | C. freundii | 128 |
| 100 | C. freundii | 128 |
| 101 | C. freundii | 128 |
| 30-106 | E. aerogenes | 128 |
| 107 | E. aerogenes | 128 |
| 109 | E. aerogenes | 128 |
| 110 | E. aerogenes | 128 |
| 112 | E. aerogenes | 128 |
| 6-74 | E. aerogenes | 128 |
| 6-86 | E. cloacae | 128 |
| 30-111 | E. cloacae | 128 |
| 30-118 | E. cloacae | 128 |
| 30-150 | E. cloacae | 128 |
| 30-123 | E. cloacae | 128 |
| 30-125 | E. cloacae | 128 |
| 88 | E. cloacae | 128 |
| 89 | E. cloacae | 128 |
| 93.1 | E. cloacae | 128 |
| 102 | E. cloacae | 128 |
| 103 | E. cloacae | 128 |
| 166 | E. cloacae | 128 |
| 168 | E. cloacae | 128 |
| 214 | E. cloacae | 128 |
| 30-97 | E. cloacae | 128 |
| 30-85 | E. cloacae | 128 |
| 92 | E. cloacae | 128 |
| 225.2 | E. cloacae | 128 |
| 6-84 | E. cloacae | 128 |
| 355 | E. coli | 16 |
| 001 | E. coli | 32 |
| 004 | E. coli | 32 |
| 359 | E. coli | 32 |
| 361.2 | E. coli | 32 |
| 6-82 | E. coli | 64 |
| 30-138 | E. coli | 64 |
| 005 | E. coli | 16 |
| 006 | E. coli | 16 |
| 015 | E. coli | 16 |
| 019 | E. coli | 16 |
| 144 | E. coli | 16 |
| 152 | E. coli | 16 |
| 20-120 | E. coli | 16 |
| 155 | E. coli | 16 |
| 320 | E. coli | 16 |
| 324 | E. coli | 16 |
| 326 | E. coli | 16 |
| 330 | E. coli | 16 |
| 332 | E. coli | 16 |
| 009 | E. coli | 32 |
| 012 | E. coli | 32 |
| 013 | E. coli | 32 |
| 036 | E. coli | 32 |
| 037 | E. coli | 32 |
| 055 | E. coli | 32 |

TABLE 3-continued

| Number | Strain | MIC (mg/L) |
|---|---|---|
| 097 | E. coli | 32 |
| 101 | E. coli | 32 |
| 104 | E. coli | 32 |
| 112 | E. coli | 32 |
| 145 | E. coli | 32 |
| 6-73 | E. coli | 32 |
| 20-124 | E. coli | 32 |
| 159 | E. coli | 32 |
| 164 | E. coli | 32 |
| 312 | E. coli | 32 |
| 313 | E. coli | 32 |
| 314 | E. coli | 32 |
| 416 | E. coli | 32 |
| 455 | E. coli | 32 |
| 113 | E. coli | 64 |
| 120 | E. coli | 64 |
| 122 | E. coli | 64 |
| 123 | E. coli | 64 |
| 124 | E. coli | 64 |
| 154 | E. coli | 64 |
| 6-56 | E. coli | 64 |
| 6-58 | E. coli | 64 |
| 6-77 | E. coli | 64 |
| 6-85 | E. coli | 64 |
| 6-95 | E. coli | 64 |
| 20-19 | E. coli | 64 |
| 20-42 | E. coli | 64 |
| 20-133 | E. coli | 64 |
| 20-135 | E. coli | 64 |
| 20-158 | E. coli | 64 |
| 165 | E. coli | 64 |
| 169 | E. coli | 64 |
| 170 | E. coli | 64 |
| 177 | E. coli | 64 |
| 192 | E. coli | 64 |
| 369 | E. coli | 64 |
| 121 | E. coli | 128 |
| 125 | E. coli | 128 |
| 30-25 | E. coli | 128 |
| 30-143 | E. coli | 128 |
| 30-4 | E. coli | 128 |
| 30-65 | E. coli | 128 |
| 20-161 | E. coli | 128 |
| 20-180 | E. coli | 128 |
| 201 | E. coli | 128 |
| 223 | E. coli | 128 |
| 256 | E. coli | 128 |
| 421 | E. coli | 128 |
| 20-26 | E. coli | 32 |
| 20-27 | E. coli | 32 |
| 122 | E. coli | 32 |
| 288 | E. coli | 32 |
| 6-64 | E. coli | 64 |
| 6-80 | E. coli | 64 |
| 6-101 | E. coli | 64 |
| 6-107 | E. coli | 64 |
| 6-94 | E. coli | 64 |
| 6-62 | E. coli | 64 |
| 30-11.1 | E. coli | 64 |
| 30-149 | E. coli | 64 |
| 30-8 | E. coli | 64 |
| 20-22 | E. coli | 64 |
| 20-29 | E. coli | 64 |
| 20-38 | E. coli | 64 |
| 20-39 | E. coli | 64 |
| 20-40 | E. coli | 64 |
| 20-63 | E. coli | 64 |
| 20-102 | E. coli | 64 |
| 20-119 | E. coli | 64 |
| 20-127 | E. coli | 64 |
| 20-156 | E. coli | 64 |
| 123 | E. coli | 64 |
| 124 | E. coli | 64 |
| 137 | E. coli | 64 |
| 423 | E. coli | 64 |
| 428 | E. coli | 64 |
| 132 | E. coli | 128 |
| 6-98 | E. coli | 128 |
| 6-110 | E. coli | 128 |
| 30-69 | E. coli | 128 |
| 30-84 | E. coli | 128 |
| 30-117 | E. coli | 128 |
| 30-128 | E. coli | 128 |
| 30-151 | E. coli | 128 |
| 30-53 | E. coli | 128 |
| 30-26.1 | E. coli | 128 |
| 20-21 | E. coli | 128 |
| 20-24 | E. coli | 128 |
| 20-177 | E. coli | 128 |
| 20-184 | E. coli | 128 |
| 20-185 | E. coli | 128 |
| 431 | E. coli | 128 |
| 6-99 | E. coli | 64 |
| 6-90 | E. coli | 64 |
| 30-15 | E. coli | 128 |
| 30-110 | E. coli | 128 |
| 6 | E. sacazakii | 128 |
| 8 | E. sacazakii | 128 |
| 9 | E. sacazakii | 128 |
| 20-35 | K. oxytoca | 64 |
| 3.1 | K. oxytoca | 64 |
| 55 | K. oxytoca | 64 |
| 7 | K. oxytoca | 64 |
| 14 | K. oxytoca | 64 |
| 6-78 | K. oxytoca | 128 |
| 3.2 | K. oxytoca | 128 |
| 65 | K. oxytoca | 128 |
| 20 | K. oxytoca | 128 |
| 30-87 | K. oxytoca | 128 |
| 6-66 | K. pneumoniae | 128 |
| 20-77 | K. pneumoniae | 128 |
| 20-126 | K. pneumoniae | 128 |
| 11 | K. pneumoniae | 128 |
| 12 | K. pneumoniae | 128 |
| 63 | K. pneumoniae | 128 |
| 118 | K. pneumoniae | 128 |
| 21 | K. pneumoniae | 128 |
| 28 | K. pneumoniae | 128 |
| 6-117 | K. pneumoniae | 128 |
| 30-124 | K. pneumoniae | 128 |
| 20-189 | K. pneumoniae | 128 |
| 13 | K. pneumoniae | 128 |
| 65 | K. pneumoniae | 128 |
| 46 | K. pneumoniae | 128 |
| 6-113 | M. morganii | 128 |
| 58 | M. morganii | 64 |
| 59 | M. morganii | 64 |
| 20-157 | M. morganii | 128 |
| 55 | M. morganii | 128 |
| 56 | M. morganii | 128 |
| 57 | M. morganii | 128 |
| 30-43 | P. mirabilis | 64 |
| 30-80 | P. mirabilis | 128 |
| 30-20.2 | P. mirabilis | 64 |
| 32 | P. mirabilis | 64 |
| 33 | P. mirabilis | 64 |
| 82 | P. mirabilis | 64 |
| 83 | P. mirabilis | 64 |
| 30-41 | P. mirabilis | 128 |
| 41 | P. mirabilis | 128 |
| 42 | P. mirabilis | 128 |
| 6-57 | P. mirabilis | 128 |
| 34 | P. mirabilis | 128 |
| 35 | P. mirabilis | 128 |
| 36 | P. mirabilis | 128 |
| 37 | P. mirabilis | 128 |
| 38 | P. mirabilis | 128 |
| 56 | P. mirabilis | 128 |
| 76 | S. liquefaciens | 128 |
| 77 | S. liquefaciens | 128 |
| 78 | S. liquefaciens | 128 |
| 99 | S. marcescens | 128 |
| 30-12 | S. marcescens | 128 |
| 30-76 | S. marcescens | 128 |
| 20-23 | S. marcescens | 128 |
| 20-70 | S. marcescens | 128 |

TABLE 3-continued

| Number | Strain | MIC (mg/L) |
|---|---|---|
| 112 | S. marcescens | 128 |
| ATCC 25922 | E. coli | 32 |
| 20-89 | A. baumannii | 32 |
| 96 | A. baumannii | 32 |
| 51 | A. baumannii | 32 |
| 30-49 | A. baumannii | 64 |
| 99 | A. baumannii | 64 |
| 20-64 | A. lwoffi | 4 |
| 20-160 | A. lwoffi | 128 |
| 20-49 | A. xyloxy | 128 |
| 50 | A. xyloxy | 128 |
| 7 | P. aeruginosa | 32 |
| 8 | P. aeruginosa | 32 |
| 9 | P. aeruginosa | 64 |
| 10 | P. aeruginosa | 16 |
| 11 | P. aeruginosa | 64 |
| 12 | P. aeruginosa | 64 |
| 13 | P. aeruginosa | 32 |
| 30-94 | S. maltophilia | 64 |
| 64 | S. maltophilia | 64 |
| 99 | S. maltophilia | 64 |
| 30-105 | S. maltophilia | 128 |
| 66 | S. maltophilia | 128 |
| 79.1 | S. maltophilia | 128 |
| 20-149 | S. maltophilia | 64 |
| 20-58 | S. maltophilia | 128 |
| 78 | S. maltophilia | 128 |
| 115 | S. maltophilia | 128 |
| ATCC 27853 | P. aeruginosa | 32 |

TABLE 4

| No. | Strain | M.I.C. (mg/ml) |
|---|---|---|
| 387.2 | S. aureus | 0.12 |
| 78 | S. aureus | 0.25 |
| 79 | S. aureus | 0.25 |
| 387.1 | S. aureus | 0.25 |
| 20-13 | S. aureus | 0.25 |
| 20-5 | S. aureus | 0.12 |
| 90 | S. aureus | 0.25 |
| 91 | S. aureus | 0.25 |
| 96 | S. aureus | 0.25 |
| 386 | S. aureus | 0.25 |
| 388 | S. aureus | 0.25 |
| 20-12 | S. aureus | 0.25 |
| 20-17 | S. aureus | 0.25 |
| 80 | S. aureus | 0.5 |
| 93 | S. aureus | 0.5 |
| 95 | S. aureus | 0.5 |
| 101 | S. aureus | 0.5 |
| 111 | S. aureus | 0.5 |
| 414 | S. aureus | 0.5 |
| 20-9 | S. aureus | 0.5 |
| 20-28 | S. aureus | 0.5 |
| 81 | S. aureus | 1 |
| 83 | S. aureus | 1 |
| 94 | S. aureus | 1 |
| 394 | S. aureus | 1 |
| 107 | S. aureus | 1 |
| 113 | S. aureus | 1 |
| 411 | S. aureus | 1 |
| 20-10 | S. aureus | 1 |
| 20-43 | S. aureus | 1 |
| 20-44 | S. aureus | 1 |
| 97 | S. aureus | 0.25 |
| 98 | S. aureus | 0.25 |
| 30-18 | S. aureus | 0.25 |
| 30-83.2 | S. aureus | 0.25 |
| 92 | S. aureus | 0.5 |
| 99 | S. aureus | 0.5 |
| 100 | S. aureus | 0.5 |
| 102 | S. aureus | 0.5 |
| 103 | S. aureus | 0.5 |
| 106 | S. aureus | 0.5 |

TABLE 4-continued

| No. | Strain | M.I.C. (mg/ml) |
|---|---|---|
| 111.3 | S. aureus | 0.5 |
| 118 | S. aureus | 0.5 |
| 224 | S. aureus | 0.5 |
| 377 | S. aureus | 0.5 |
| 395 | S. aureus | 0.5 |
| 406 | S. aureus | 0.5 |
| 20-6 | S. aureus | 0.5 |
| 20-117 | S. aureus | 0.5 |
| 20-25 | S. aureus | 0.5 |
| 20-30 | S. aureus | 0.5 |
| 20-34 | S. aureus | 0.5 |
| 20-37 | S. aureus | 0.5 |
| 20-45 | S. aureus | 0.5 |
| 396 | S. aureus | 1 |
| 20-109 | S. aureus | 1 |
| 20-31 | S. aureus | 1 |
| 217 | S. aureus | 0.5 |
| 30-104 | S. aureus | 0.5 |
| 30-122 | S. aureus | 0.5 |
| 30-70 | S. aureus | 0.5 |
| 116 | S. aureus | 1 |
| 117 | S. aureus | 1 |
| 119 | S. aureus | 1 |
| 120 | S. aureus | 1 |
| 122 | S. aureus | 1 |
| 124 | S. aureus | 1 |
| 132 | S. aureus | 1 |
| 135 | S. aureus | 1 |
| 209 | S. aureus | 1 |
| 217 | S. aureus | 1 |
| 220 | S. aureus | 1 |
| 30-5 | S. aureus | 1 |
| 30-6 | S. aureus | 1 |
| 20-33 | S. aureus | 1 |
| 30-100 | S. aureus | 1 |
| 30-101 | S. aureus | 1 |
| 30-102 | S. aureus | 1 |
| 30-64 | S. aureus | 1 |
| 30-67 | S. aureus | 1 |
| 223 | S. aureus | 1 |
| 400 | S. aureus | 1 |
| 402 | S. aureus | 1 |
| 30-120 | S. aureus | 1 |
| 30-130 | S. aureus | 1 |
| 30-133 | S. aureus | 1 |
| 30-146 | S. aureus | 1 |
| 30-23 | S. aureus | 1 |
| 30-48 | S. aureus | 1 |
| 30-99 | S. aureus | 1 |
| 30-108 | S. aureus | 1 |
| 30-142 | S. aureus | 1 |
| 218 | S. aureus | >1 |
| 219 | S. aureus | >1 |
| 403.2 | S. aureus | >1 |
| 30-119 | S. aureus | >1 |
| 398 | S. aureus | >1 |
| 229 | S. aureus | >1 |
| 230 | S. aureus | >1 |
| 30-105 | S. aureus | >1 |
| 30-11.1 | S. aureus | >1 |
| 30-139 | S. aureus | >1 |
| 30-156 | S. aureus | >1 |
| 30-22 | S. aureus | >1 |
| 30-24 | S. aureus | >1 |
| 30-27 | S. aureus | >1 |
| 30-34 | S. aureus | >1 |
| 30-35 | S. aureus | >1 |
| 30-40 | S. aureus | >1 |
| 30-89 | S. aureus | >1 |
| 30-9.1 | S. aureus | >1 |
| 300 | S. aureus | 0.25 |
| 306 | S. aureus | 0.25 |
| 312 | S. aureus | 0.25 |
| 325 | S. aureus | 0.5 |
| 329.2 | S. aureus | 0.25 |
| 333 | S. aureus | 0.25 |
| 358 | S. aureus | 0.5 |
| 376 | S. aureus | 0.5 |

TABLE 4-continued

| No. | Strain | M.I.C. (mg/ml) |
|---|---|---|
| 16 | S. epidermidis | 0.06 |
| 20 | S. epidermidis | 0.06 |
| 20-32 | S. epidermidis | 0.06 |
| 30-16 | S. epidermidis | 0.06 |
| 19 | S. epidermidis | 0.12 |
| 7 | S. epidermidis | 0.25 |
| 9 | S. epidermidis | 0.25 |
| 11 | S. epidermidis | 0.25 |
| 41 | S. epidermidis | 0.25 |
| 42 | S. epidermidis | 0.25 |
| 20-101 | s. epidermidis | 0.25 |
| 20-104 | s. epidermidis | 0.25 |
| 20-18 | s. epidermidis | 0.25 |
| 20-61 | s. epidermidis | 0.25 |
| 20-62 | s. epidermidis | 0.25 |
| 10 | S. epidermidis | 0.5 |
| 20-107 | s. epidermidis | 0.5 |
| 12 | S. epidermidis | 0.06 |
| 30-134 | S. epidermidis | 0.06 |
| 30-75 | S. epidermidis | 0.06 |
| 17 | S. epidermidis | 0.12 |
| 30-54 | S. epidermidis | 0.12 |
| 30-55 | S. epidermidis | 0.12 |
| 30-77 | S. epidermidis | 0.12 |
| 30-90 | S. epidermidis | 0.12 |
| 30-152 | S. epidermidis | 0.5 |
| 13 | S. epidermidis | 1 |
| 30-73 | S. epidermidis | 1 |
| 30-10 | S. epidermidis | >1 |
| 30-148 | S. epidermidis | 0.5 |
| 30-135 | S. epidermidis | 1 |
| 30-109 | S. epidermidis | 0.25 |
| 29 | S. epidermidis | 0.5 |
| 36 | S. epidermidis | 0.5 |
| 30-115 | S. epidermidis | 1 |
| 37 | S. epidermidis | 1 |
| 30-92 | S. epidermidis | >1 |
| 30-78 | S. epidermidis | 1 |
| 30-154 | S. epidermidis | >1 |
| 30-2 | S. epidermidis | >1 |
| 30-66 | S. epidermidis | >1 |
| 233 | S. epidermidis | 0.06 |
| 258 | S. epidermidis | 0.06 |
| 247 | S. epidermidis | 0.06 |
| 248.1 | S. epidermidis | 0.06 |
| 266 | S. epidermidis | 0.5 |
| 64 | S. haemoliticus | 0.25 |
| 75.1 | S. haemoliticus | 0.25 |
| 65 | S. haemoliticus | 0.5 |
| 69 | S. haemoliticus | 0.5 |
| 74 | S. haemoliticus | 0.5 |
| 72 | S. haemoliticus | 1 |
| 73 | S. haemoliticus | 1 |
| 178 | S. haemoliticus | 1 |
| 20-54 | S. haemoliticus | 1 |
| 129 | S. hominis | 0.25 |
| 131 | S. hominis | 0.25 |
| 168 | S. hominis | 0.25 |
| 30-13 | S. hominis | 0.5 |
| 30-93 | S. hominis | 0.12 |
| 116.1 | S. hominis | 0.25 |
| 133 | S. hominis | 0.25 |
| 128 | S. hominis | 0.5 |
| 30-114 | S. hominis | 1 |
| 84 | S. intermedius | 1 |
| 105 | S. intermedius | 1 |
| 90 | S. intermedius | >1 |
| 30-83.1 | S. intermedius | >1 |
| 106.2 | S. intermedius | 1 |
| 83.2 | S. intermedius | >1 |
| 30-81 | S. warneri | 0.12 |
| 156 | S. warneri | 0.25 |
| 30-129 | S. warneri | 0.12 |
| 221 | S. warneri | 0.5 |
| 30-153 | S. warneri | 0.5 |
| 189.1 | S. warneri | 1 |
| 159 | S. warneri | 0.5 |
| 30-116 | S. warneri | 1 |
| 146 | S. warneri | 1 |
| 150 | S. warneri | 1 |
| 151 | S. warneri | 1 |
| 162 | S. warneri | 1 |
| 182 | S. warneri | 1 |
| 153 | S. warneri | >1 |
| 30-145 | S. warneri | >1 |
| ATCC29213 | S. aureus | 0.5 |
| 09-85 | E. faecalis | 4 |
| 035-52 | E. faecalis | 128 |
| 80 | E. faecalis | 32 |
| 81 | E. faecalis | 32 |
| 035-63 | E. faecalis | 64 |
| 035-65 | E. faecalis | 64 |
| 035-78 | E. faecalis | 64 |
| 09-35 | E. faecalis | 64 |
| 035-125 | E. faecalis | 64 |
| 82 | E. faecalis | 64 |
| 88 | E. faecalis | 64 |
| 91 | E. faecalis | 64 |
| 173 | E. faecalis | 64 |
| 188 | E. faecalis | 64 |
| 218 | E. faecalis | 64 |
| 219 | E. faecalis | 64 |
| 035-58 | E. faecalis | 128 |
| 035-116.2 | E. faecalis | 128 |
| 035-20.3 | E. faecalis | 128 |
| 87 | E. faecalis | 128 |
| 89 | E. faecalis | 128 |
| 90 | E. faecalis | 128 |
| 035-96 | E. faecalis | 64 |
| 92 | E. faecalis | 64 |
| 94 | E. faecalis | 64 |
| 09-7 | E. faecalis | 128 |
| 09-21 | E. faecalis | 128 |
| 93 | E. faecalis | 128 |
| 09-75 | E. faecalis | 128 |
| 09-94 | E. faecalis | 128 |
| 035-128.1 | E. faecalis | 128 |
| 035-136 | E. faecalis | 128 |
| 126 | E. faecalis | 128 |
| 127 | E. faecalis | 128 |
| 128 | E. faecalis | 128 |
| 158 | E. faecalis | 128 |
| 09-72 | E. faecalis | 128 |
| 169 | E. faecalis | 128 |
| 09-79 | E. faecalis | 128 |
| 172 | E. faecalis | 128 |
| 166 | E. faecalis | 128 |
| 3.2 | E. faecalis | 128 |
| 321 | E. faecalis | 128 |
| 322 | E. faecalis | 128 |
| 304 | E. faecalis | 128 |
| 307 | E. faecalis | 128 |
| 309 | E. faecalis | 128 |
| 322 | E. faecalis | 128 |
| 337 | E. faecalis | 128 |
| 335 | E. faecalis | 128 |
| 144 | E. faecalis | 128 |
| 035-35 | E. faecium | 128 |
| 035-45.2 | E. faecium | 128 |
| 035-8.2 | E. faecium | 64 |
| 100 | E. faecium | 64 |
| 106 | E. faecium | 64 |
| 09-86 | E. faecium | 128 |
| 99 | E. faecium | 128 |
| 136 | E. faecium | 64 |
| 141 | E. faecium | 64 |
| 09-68 | E. faecium | 128 |
| 035-106 | E. faecium | 128 |
| 112 | E. faecium | 128 |
| 117 | E. faecium | 64 |
| 035-97 | E. faecium | 128 |
| 126 | E. faecium | 64 |
| 138 | E. faecium | 64 |
| 169 | E. faecium | 64 |
| 188 | E. faecium | 64 |
| 197.2 | E. faecium | 64 |

TABLE 4-continued

| No. | Strain | M.I.C. (mg/ml) |
|---|---|---|
| 206 | *E. faecium* | 128 |
| | ATCC 29212 | 64 |

Example 4

A patient suffering from a bacterial infection is identified. A pharmaceutical formulation containing (16Z,18E,28E)-25-(acetyloxy)-5,21,23-trihydroxy-16-(hydroxymethyl)-27-methoxy-2,4,11,20,22,24,26-heptamethyl-1,15-dioxo-1,13-dihydro-2H-2,7-(epoxypentadeca[1,11,13]trienoimino)furo[2",3":7',8']naphto[1',2':4,5]imidazo[1,2-a]pyridine-8-ium-6-olate (Compound I, where R is acetyl, $R_1$ is hydrogen, $R_2$ methyl and $R_3$ is hydroxymethyl) is administered to the patient. Following a 10 day course of treatment using the above formulation, the level of bacterial infection in the patient is reduced.

Example 5

Alternative compounds of Formula I are synthesized according to the following process. In particular, this process is used to prepare compounds of formula I, wherein R is acetyl, $R_1$ is one of ($C_{1-4}$) alkyl, benzyloxy, mono- and di-($C_{1-3}$) alkylamino ($C_{1-4}$) alkyl, ($C_{1-3}$) alkoxy-($C_{1-4}$)alkyl, hydroxy-methyl, hydroxy-($C_{2-4}$)-alkyl, and nitro and $R_2$ is one of ($C_{1-4}$) alkyl, benzyloxy, mono- and di-($C_{1-3}$) alkylamino ($C_{1-4}$) alkyl, ($C_{1-3}$) alkoxy-($C_{1-4}$)alkyl, hydroxy-methyl, hydroxy-($C_{2-4}$)-alkyl, and nitro, or $R_1$ and $R_2$ taken together with two consecutive carbon atoms of the pyridine nucleus form a benzene ring unsubstituted, or mono-substituted or di-substituted by methyl or ethyl, and $R_3$ one of is hydroxyethyl, hydroxypropyl or hydroxybutyl.

A solution of 200 mg of Formula II, produced substantially as disclosed in Example 1, is dissolved in 0.6 ml distilled water and 0.5 ml ethanol, added under stirring at room temperature with 82 mg of a 2-amino-pyridine of Formula III, substituted by one or two of the following substituents at the $R_1$ or $R_2$ positions: ($C_{1-4}$) alkyl, benzyloxy, mono- and di-($C_{1-3}$) alkylamino ($C_{1-4}$) alkyl, ($C_{1-3}$) alkoxy-($C_{1-4}$)alkyl, hydroxy-methyl, hydroxy-($C_{2-4}$)-alkyl, and nitro and $R_2$ is one of ($C_{1-4}$) alkyl, benzyloxy, mono- and di-($C_{1-3}$) alkylamino ($C_{1-4}$) alkyl, ($C_{1-3}$) alkoxy-($C_{1-4}$)alkyl, hydroxy-methyl, hydroxy-($C_{2-4}$)-alkyl, and nitro, or substituted such that $R_1$ and $R_2$, taken together with two consecutive carbon atoms of the pyridine nucleus, form a benzene ring unsubstituted, or mono-substituted or di-substituted by methyl or ethyl. The reaction mixture is kept at a temperature of 47° C. for about five hours until disappearance of the reagent of Formula II by HPLA analysis in the same reported in Example 1. The solution is brought to ambient temperature and 5 mg of ascorbic acid is added. The solution is acidified to pH 2.0 with concentrated HCL and then the solution is extracted with two aliquots of about 1.0 ml of ethylene acetate. The pooled organic phases are dried over sodium sulfate, filtered and evaporated by dryness. The obtained compound is characterized in HPLC, as described in Example 1. The obtained compound of Formula I, after complete reaction, is characterized by a RT. The obtained compound is identified in FT-IR, $^1$H-NMR, $^{13}$C-NMR spectroscopy and the molecular weight is determined with EIMS spectroscopy.

Example 6

Alternative compounds of Formula I are produced according to the following process. In particular, this process is used to prepare compounds of formula I, wherein R is acetyl, $R_1$ is one of ($C_{1-4}$) alkyl, benzyloxy, mono- and di-($C_{1-3}$) alkylamino ($C_{1-4}$) alkyl, ($C_{1-3}$) alkoxy-($C_{1-4}$)alkyl, hydroxy-methyl, hydroxy-($C_{2-4}$)-alkyl, and nitro and R2 is one of ($C_{1-4}$) alkyl, benzyloxy, mono- and di-($C_{1-3}$) alkylamino ($C_{1-4}$) alkyl, ($C_{1-3}$) alkoxy-($C_{1-4}$)alkyl, hydroxy-methyl, hydroxy-($C_{2-4}$)-alkyl, and nitro, or $R_1$ and $R_2$ taken together with two consecutive carbon atoms of the pyridine nucleus form a benzene ring unsubstituted, or mono-substituted or di-substituted by methyl or ethyl, and $R_3$ one of is hydroxyethyl, hydroxypropyl or hydroxybutyl.

A culture of *Nocardia mediterranea* (ATCC 31064) is propagated for 6-8 days on Benett's agar and incubated at 28° C. With the culture obtained from the agar slant, two 500 ml Erlenmeyer flask are inoculated under sterile conditions. The flasks contain 100 ml of vegetative medium composition as described in Table 1 in Example 1.

The pH is adjusted to 7.3 with 1M NaOH. The flasks so inoculated are placed on an alternative shaker at 28° C. for 72 hours. The content of the two Erlenmeyer flasks is used as inoculum by pouring it in a 10-liter pre-fermenter, containing 4 liters of the above mentioned vegetative medium. The incubation is carried out at 28° C. with an agitation of 300 r.p.m. and 1 v/v/m aeration. After 48 hours of growth a volume of 7-10% of packed cell is obtained.

In the next stage the cells are used as an inoculum in a 10 liter glass fermenter containing 4 liters of medium composition as described below and in Table 2 in Example 1.

The pH is adjusted to 7.8 with NaOH and sterilized for 60 minutes at 120° C. After sterilization the pH is 6.4. An amount of the prefermenter content equal to 5% of the fermenter content is used as an inoculum. The fermentation is carried out at 28° C. with a 750 r.p.m. agitation and aerating at a rate of 1/v/v/m. Silicone A is used as antifoam. The culture broth turns to a characteristic red-brown color during the fermentation. After about 200 hours of growth a volume of packed cells is obtained. The pH of the broth is 7.5, and the broth is then harvested to remove the cells.

The mycelium is removed by filtration and discarded. The filtrate is adjusted to pH 2.0 with 10% (v/v) hydrochloric acid and extracted three times with an equal volume of ethylacetate. The combined extracts are concentrated to dryness under vacuum at 35° C. and the residue is dissolved in 0.005 M sodium phosphate buffer pH 7.5. Sodium nitrite is added to give a final concentration of 0.2% (w/v). After stirring for 30 min. at room temperature the buffer solution is extracted three times with an equal volume of ethyl acetate. The combined organic extracts are concentrated to dryness under vacuum at 35° C. The extract is purified using silica gel column chromatography as the same condition of Example 1.

The obtained compound, having RT of 7.45 min is dissolved in 0.6 ml distilled water and 0.5 ml ethanol are added under stirring at room temperature with 82 mg of 2-amino-4-methyl-pyridine. The reaction mixture is kept at 47° C. for about five hours until complete disappearance of the reagent of Formula II by HPLC analysis in the same reported in Example 1. The solution is brought to ambient temperature and 5 mg of ascorbic acid is added. The solution is acidified to pH 2.0 with concentrated HCL and than the solution is extracted with two aliquots of about 1.0 ml of ethylene acetate. The pooled organic phases are dried over sodium sulfate, filtered and evaporated by dryness.

The obtained compound is analyzed in HPLC in the same condition of Example 1, is characterized by a RT of 6.2 min., with a purity corresponding to 95%.

We claim:

1. A pharmaceutical composition comprising a therapeutically effective amount of one or more compounds of Formula I and a pharmaceutically acceptable carrier comprising one or more pharmaceutically acceptable excipients; wherein the one or more compounds of Formula I has the structure:

I wherein:
R is hydrogen or acetyl,
$R_1$ and $R_2$ are each independently either hydrogen or ($C_{1-4}$)alkyl, and
$R_3$ is hydroxyalkyl ($C_{1-4}$).

2. The pharmaceutical composition according to claim 1, wherein, for the one or more compounds of Formula I, R is a hydrogen or acetyl group, $R_1$ and $R_2$ are independently hydrogen or methyl, and $R_3$ is hydroxyalkyl ($C_{1-4}$).

3. The pharmaceutical composition according to claim 2, wherein R is an acetyl group, $R_1$ is hydrogen, $R_2$ is methyl and $R_3$ is hydroxymethyl.

4. The pharmaceutical composition according to claim 1, further comprising one or more compounds of Formula II having the structure:

II wherein R is acetyl or hydrogen, and $R_3$ is hydroxyalkl ($C_1$-$C_4$).

5. The pharmaceutical composition according to claim 4, wherein, for the one or more compounds of Formula I, R is an acetyl group, $R_1$ is hydrogen, $R_2$ is methyl and $R_3$ is hydroxymethyl; and wherein, for the one or more compounds of Formula II, R is an acetyl group and $R_3$ is hydroxymethyl.

6. The pharmaceutical composition according to claim 4, wherein the combination of the one or more compounds of Formula I and the one or more compounds of Formula II is from 0.5 to 90% with respect to the pharmaceutically acceptable carrier.

7. The pharmaceutical composition according to claim 4, wherein the amount of the one or more compounds of Formula I present in the pharmaceutical composition is less than the amount of the one or more compounds of Formula I that would be present when the one or more compounds of Formula II is not also administered.

8. The pharmaceutical composition according to claim 1, wherein the composition is a pharmaceutically-acceptable formulation suitable for oral, nasal, topical, rectal, vaginal, aerosol or parenteral administration.

9. The pharmaceutical composition according to claim 1, further comprising one or more additional antibiotics, wherein the amount of the one or more compounds of Formula I present in the pharmaceutical composition is less than the amount of the one or more compounds of Formula I that would be present when the one or more additional antibiotics are not also administered.

10. The pharmaceutical composition of according to claim 9, wherein the one or more additional antibiotics is selected from rifamycin, rifaximin, and neomycin.

11. The pharmaceutical composition of according to claim 10, wherein the one or more additional antibiotics is rifaximin.

12. The pharmaceutical composition according to claim 11, wherein the composition is formulated for oral administration and is administered in a single or in a separate dosage form.

13. The pharmaceutical composition according to claim 11, wherein the one or more compounds of Formula I is in a ratio from about 0.01 to 100% (w/w) with respect to the one or more additional antibiotics.

14. The pharmaceutical composition according to claim 9, further comprising one or more compounds of Formula II having the structure:

II wherein R is acetyl or hydrogen, and $R_3$ is hydroxyalkl ($C_{1-4}$).

15. The pharmaceutical composition of claim 11, wherein the combination of the one or more compounds of Formula I is in an amount from 0.5 to 90% with respect to the pharmaceutically acceptable carrier.

16. The pharmaceutical composition according to claim 11, wherein the composition is a pharmaceutically-acceptable formulation suitable for oral, nasal, topical, rectal, vaginal, aerosol or parenteral administration.

17. The pharmaceutical composition according to claim 16, wherein the composition is formulated for oral administration, and wherein the composition is in a form selected from capsules, cachets, pills, tablets, lozenges, powders, granules, a solution, a suspension, an oil-in-water emulsion, a water-in-oil liquid emulsion, an elixir, a syrup, pastilles and mouth washes.

18. The pharmaceutical composition according to claim 16, wherein the composition is formulated for topical administration and wherein the composition is in a form selected from ointments, pomades, creams, gels, sprays and lotions.

19. The pharmaceutical composition according to claim 16, wherein the composition is formulated for vaginal or rectal administration and wherein the composition is in a form selected from a pessary, cream, foam, aerosol and spray.

20. The pharmaceutical composition according to claim 16, wherein the composition is formulated to provide sustained delivery to a subject for at least 12 hours, 24 hours, 36 hours, 48 hours, one week, two weeks, three weeks, or four weeks after the formulation is administered to the subject.

21. A method of treating a bowel related disorder associated with bacterial overgrowth in a patient in need thereof, said method comprising administering to the patient the composition of claim 11.

22. The method according to claim 21, wherein the bowel related disorder is one or more of irritable bowel syndrome, travelers' diarrhea, small intestinal bacterial overgrowth, Crohn's disease, chronic pancreatitis, pancreatic insufficiency, hepatic encephalopathy, diverticulitis, enteritis, or colitis.

23. The method according to claim 22, wherein the composition is formulated for oral administration, and wherein the composition is in a form selected from capsules, cachets, pills, tablets, lozenges, powders, granules, a solution, a suspension, an oil-in-water emulsion, a water-in-oil liquid emulsion, an elixir, a syrup, and pastilles.

24. The method according to claim 23, wherein the composition is administered in a single dose or in a separate dose form.

25. The method according to claim 24, wherein the composition is administered in a separate dose form, and wherein the period of time between administration of each dose form is from less than 5 minutes up to 120 hours.

26. The method according to claim 22, wherein the dosage range of the one or more compounds of Formula I is from 1 to 3000 mg per day.

27. The method according to claim 22, wherein the dose of the one or more compounds of Formula I is from about 1 mg to about 200 mg per kg of body weight.

28. The method according to claim 27, wherein the dose is about 10 mg to about 100 mg per kg of body weight.

29. The method according to claim 28, wherein the dose is about 40 mg to about 80 mg per kg of body weight.

* * * * *